United States Patent
Purcell Ngambo et al.

(10) Patent No.: US 10,251,938 B2
(45) Date of Patent: Apr. 9, 2019

(54) ANGIOPOIETIN-BASED INTERVENTIONS FOR TREATING CEREBRAL MALARIA

(71) Applicants: Regeneron Pharmaceuticals, Inc., Tarrytown, NY (US); University Health Network, Toronto (CA)

(72) Inventors: Lisa Arleen Purcell Ngambo, Garnerville, NY (US); Sarah J. Higgins, Toronto (CA); Kevin C. Kain, Toronto (CA)

(73) Assignees: Regeneron Pharmaceuticals, Inc., Tarrytown, NY (US); University Health Network, Toronto (CA)

( * ) Notice: Subject to any disclaimer, the term of this patent is extended or adjusted under 35 U.S.C. 154(b) by 0 days.

(21) Appl. No.: 15/949,472

(22) Filed: Apr. 10, 2018

(65) Prior Publication Data
US 2018/0228870 A1    Aug. 16, 2018

Related U.S. Application Data

(62) Division of application No. 15/414,925, filed on Jan. 25, 2017, now Pat. No. 9,968,653, which is a division of application No. 14/529,677, filed on Oct. 31, 2014, now Pat. No. 9,592,271.

(60) Provisional application No. 62/040,514, filed on Aug. 22, 2014, provisional application No. 61/898,539, filed on Nov. 1, 2013.

(51) Int. Cl.
| *A61K 31/49* | (2006.01) |
| *A61K 38/18* | (2006.01) |
| *A61K 38/16* | (2006.01) |
| *A61K 38/17* | (2006.01) |
| *A61K 39/395* | (2006.01) |
| *C07K 16/22* | (2006.01) |
| *A61K 45/06* | (2006.01) |
| *A61K 31/357* | (2006.01) |
| *A61K 31/365* | (2006.01) |
| *C07K 14/515* | (2006.01) |
| *A61K 39/00* | (2006.01) |

(52) U.S. Cl.
CPC ........ *A61K 38/1891* (2013.01); *A61K 31/357* (2013.01); *A61K 31/365* (2013.01); *A61K 31/49* (2013.01); *A61K 38/16* (2013.01); *A61K 38/17* (2013.01); *A61K 38/18* (2013.01); *A61K 38/1866* (2013.01); *A61K 39/3955* (2013.01); *A61K 45/06* (2013.01); *C07K 14/515* (2013.01); *C07K 16/22* (2013.01); *A61K 2039/505* (2013.01); *A61K 2039/54* (2013.01); *A61K 2039/545* (2013.01); *C07K 2319/30* (2013.01); *Y02A 50/386* (2018.01); *Y02A 50/412* (2018.01)

(58) Field of Classification Search
None
See application file for complete search history.

(56) References Cited

U.S. PATENT DOCUMENTS

| 7,008,781 | B1 | 3/2006 | Davis et al. |
| 9,592,271 | B2 | 3/2017 | Purcell Ngambo et al. |
| 9,968,653 | B2 | 5/2018 | Purcell Ngambo et al. |
| 2011/0027286 | A1 | 2/2011 | Thurston et al. |
| 2012/0189635 | A1 | 7/2012 | Thurston et al. |
| 2014/0112930 | A1 | 4/2014 | Thurston et al. |

FOREIGN PATENT DOCUMENTS

| WO | 06/035319 A2 | 4/2006 |
| WO | 07/033216 A2 | 3/2007 |
| WO | 11/093851 A1 | 8/2011 |
| WO | 13/028442 A1 | 2/2013 |
| WO | 15/066426 A2 | 5/2015 |

OTHER PUBLICATIONS https://en.wikipedia.org/wiki/Artesunate 2007.*
Baptista et al., "Accumulation of Plasmodium berghei-Infected Red Blood Cells in the Brain Is Crucial for the Development of Cerebral Malaria in Mice," Infect. Immun, 78(9):4033-4039, (2010).
Benest et al., "Angiopoietin-2 Is Critical for Cytokine-Induced Vascular Leakage," PLoS ONE, 8(8):e70459, DOI: 10.1371/journal.pone.0070459, 9 pages, (2013).
Bienvenu et al. "Effect of Exogenous Angiopoietin During Experimental Cerebral Malaria," American Journal of Tropical Medicine & Hygiene, American Society of Tropical Medicine and Hygiene. 81(5):43-43, (2009).
Brouwers et al., "Platelet Activation Determines Angiopoietin-1 and VEGF Levels in Malaria: Implications for Their Use as Biomarkers," PLoS ONE, 8(6):e64850, DOI:10.1371/journal.pone. 00641850, (2013).
Carvalho et al., "Vascular dysfunction as a target for adjuvant therapy in cerebral malaria," Mem Inst Oswaldo Cruz, 109(5):577-588, (2014).
Chothia et al. "The relation between the divergence of sequence and structure in proteins," The EMBO Journal, 5(4):823-826, (1986).
Conroy et al., "Angiopoietin-2 levels are associated with retinopathy and predict mortality in Malawian children with cerebral malaria: A retrospective case—control study," Crit Care Med, 40(3):952-959, (2012).

(Continued)

*Primary Examiner* — Jennifer E Graser

(74) *Attorney, Agent, or Firm* — Schwabe, Williamson & Wyatt PC; Apama G. Patankar

(57) ABSTRACT

The present invention provides methods for treating, preventing or reducing the severity of cerebral malaria. The methods of the present invention comprise administering to a subject in need thereof a therapeutically effective amount of a pharmaceutical composition comprising a modified angiopoietin molecule such as AngF1-Fc-F1.

16 Claims, 21 Drawing Sheets

Specification includes a Sequence Listing.

(56) References Cited

OTHER PUBLICATIONS

Conroy et al., "Whole blood angiopoietin-1 and -2 levels discriminate cerebral and severe (non-cerebral) malaria from uncomplicated malaria," Malaria Journal, 8:295, DOI: 10.1 186/1475-2875-8-295, 7 pages, (2009).
Davis et al., "Angiopoietins have distinct modular domains essential for receptor binding, dimerization and superclustering," Nature Structural Biology, 10(1):38-44, 146, (2003). [Corrigendum, Nature Structural Biology, 10(2):146-146, (2003)].
De Oca et al., "Plasmodium berghei ANKA (PbA) Infection of C57BL/6J Mice: A Model of Severe Malaria," Methods in Molecular Biology, 1031:203-213, (2013).
Finney et al., "S1P Is Associated with Protection in Human and Experimental Cerebral Malaria," Mol Med, 17(7-8):717-725, (2011).
Greenspan et al. "Defining epitopes: It's not as easy as it seems," Nature Biotechnology, 17:936-937, (1999).
Higgins et al., "Immunopathogenesis of falciparum malaria: implications for adjunctive therapy in the management of severe and cerebral malaria," Expert Rev. Anti Infect. Ther., 9(9):803-819, (2011).
Idro et al., "Cerebral Malaria; Mechanisms of Brain Injury and Strategies for Improved Neuro-Cognitive Outcome," Europe PMC Funders Group, Author Manuscript, Pediatr Res. Author manuscript; available in PMC Apr. 1, 2011, vol. 68(4):267-274, Oct. 2010.
John et al., "Adjunctive therapy for cerebral malaria and other severe forms of Plasmodium falciparum malaria," Expert Rev Anti Infect Ther, 8(9):997-1008, (2010).
Kim et al., "Endothelial activation and dysregulation in malaria: a potential target for novel therapeutics," Curr Opin Hematol, 18:177-185, (2011).
Lee et al., "COMP-Angl, Angiopoietin-1 Variant Protects Radiation-Induced Bone Marrow Damage in C57BL/6 Mice," J. RadiaL Res, 49(3):313-320, (2008).
Lovegrove et al., "Serum Angiopoietin-1 and -2 Levels Discriminate Cerebral Malaria from Uncomplicated Malaria and Predict Clinical Outcome in African Children," PLoS ONE, 4(3):e4912, DOI: 10.1371/journal.pone.00049128, 8 pages, (2009).
Lovegrove et al., "Simultaneous host and parasite expression profiling identifies tissue-specific transcriptional programs associated with susceptibility or resistance to experimental cerebral malaria," BMC Genomics, 7:295, DOI: 10.1186/1471-2164-7-295, 17 pages, (2006).
Mikayama et al. "Molecular cloning and functional expression of a cDNA encoding glycosylation-inhibiting factor," Proc. Natl. Acad. Sci. USA, 90:10056-10060, (1993).
Ong et al., "Differential regulation of angiopoietin 1 and angiopoietin 2 during dengue virus infection of human umbilical vein endothelial cells: implications for endothelial hyperpermeability," Med Microbiol Immunol, DOI: 10.1007/s00430-013-0310-5, 16 pages, (2013). [Published online].
Page et al., "Biomarkers of endothelial activation/dysfunction in infectious diseases," Virulence, 4(6):507-516, (2013).
Page, et al., "Dysregulation of Angiopoietin 1 and 2 in *Escherichia coli* O157:H7 Infection and the Hemolytic-Uremic Syndrome," JID, 208:929-933, (2013).
Parikh et al., "Dysregulation of the angiopoietin-Tie-2 axis in sepsis and ARDS," Virulence, 4(6):517-524, (2013).
Prapansilp et al., "A clinicopathological correlation of the expression of the angiopoietin-Tie-2 receptor pathway in the brain of adults with Plasmodium faiciparum malaria," Malaria Journal, 12:50, 15 pages, DOI: 10 1186/1475-2875-12-50, (2013).
Rudinger et al. "Characteristics of the amino acids as components of a peptide hormone sequence," Peptide Hormones, Biological Council, pp. 1-7, (1976).
Salcedo et al., "The Potential of Angiogenesis Soluble Markers in Chronic Hepatitis C," Hepatology, 42(3):696-701, (2005).
Souza et al., "Early and late acute lung injury and their association with distal organ damage in murine malaria," Respiratory Physiology & Neurobiology, 186:65-72, (2013).
Suri et al., "Increased Vascularization in Mice Overexpressing Angiopoietin-1," Science, 282:468-471, (1998).
Tabruyn et al., "Angiopoietin-2-Driven Vascular Remodeling in Airway Inflammation," Am J Pathol, 177 (6):3233-3244, (2010).
Thurston et al., "Angiopoietin-1 protects the adult vasculature against plasma leakage," Nature Medicine, 6(4):460-463, (2000).
Thurston et al., "Leakage-Resistant Blood Vessels in Mice Transgenically Overexpressing Angiopoietin-1," Science, 286:2511-2514, (1999).
U.S. Appl. No. 14/529,677, Non-Final Office Action dated May 18, 2016.
U.S. Appl. No. 14/529,677, Notice of Allowance dated Oct. 26, 2016.
U.S. Appl. No. 14/529,677, Requirement for Restriction/Election dated Jan. 20, 2016.
U.S. Appl. No. 15/414,925, Non-Final Office Action dated May 3, 2017.
U.S. Appl. No. 15/414,925, Notice of Allowance dated Jan. 10, 2018.
Van De Weg et al., "Serum angiopoietin-2 and soluble VEGF receptor 2 are surrogate markers for plasma leakage in patients with acute dengue virus infection," J Clin Virol, 8 pages, (2014). [Retrieved from the Internet: <URL: http://dx.doi.org/10.1016/j.jcv.2014.05.001>].
WIPO Application No. PCT/US2014/063347, PCT International Preliminary Report on Patentability dated May 3, 2016.
WIPO Application No. PCT/US2014/063347, PCT International Search Report and Written Opinion of the International Searching Authority dated May 22, 2015.
WIPO Application No. PCT/US2014/063347, PCT Invitation to Pay Additional Fees dated Mar. 2, 2015.
Yeo et al., "Angiopoietin-2 is associated with decreased endothelial nitric oxide and poor clinical outcome in severe falciparum malaria," PNAS, 105(44):17097-17102, (2008).
Zhang et al., "Angiopoietin-1 Reduces Cerebral Blood Vessel Leakage and Ischemic Lesion Volume After Focal Cerebral Embolic Ischemia in Mice," Neuroscience, 113(3):683-687, (2002).
Zhang et al., "Vascular Endothelial Growth Factor and Angiopoietins in Focal Cerebral Ischemia," TCM, 12(2):62-66, (2002).
Cho et al., "Comp-Ang1: A designed angiopoietin-1 variant with nonleaky angiogenic activity," PNAS, vol. 101 (No. 15):5547-5552 (Apr. 13, 2004). [Retrieved from the Internet Jul. 26, 2018: <URL: http://www.pnas.org/cgi/doi/10.1073/pnas.0307574101>].
The American Journal of Tropical Medicine and Hygiene, vol. 87 (No. 5 Supplement): p. 439, (Nov. 2012).
U.S. Appl. No. 61/898,539, filed Nov. 1, 2013, Expired.
U.S. Appl. No. 62/040,514, filed Aug. 22, 2014, Expired.
U.S. Appl. No. 14/529,677, filed Oct. 31, 2014, U.S. Pat. No. 9,592,271, Issued.
PCT/US2014/063347, Oct. 31, 2014, WO 15/066426, Expired.
U.S. Appl. No. 15/414,925, filed Jan. 25, 2017, U.S. Pat. No. 9,968,653, Issued.

\* cited by examiner

ANGIOPOIETIN-BASED INTERVENTIONS FOR TREATING CEREBRAL MALARIA

CROSS-REFERENCE TO RELATED APPLICATIONS

This application is a division of U.S. application Ser. No. 15/414,925, filed Jan. 25, 2017, now U.S. Pat. No. 9,968,653, which is a division of U.S. application Ser. No. 14/529,677, filed Oct. 31, 2014, now U.S. Pat. No. 9,592,271, which claims the benefit under 35 USC § 119(e) of U.S. Provisional Application No. 61/898,539, filed on Nov. 1, 2013, and 62/040,514, filed on Aug. 22, 2014, the disclosures of which are each herein incorporated by reference in their entireties.

SEQUENCE LISTING

This application includes an electronic sequence listing in a file named "A0007US03-Sequence.txt", created on Apr. 10, 2018 and containing 16,602 bytes, which is hereby incorporated by reference in its entirety for all purposes.

FIELD OF THE INVENTION

The present invention relates to the use of angiopoietin molecules or variants thereof to treat or prevent cerebral malaria in a subject in need thereof.

BACKGROUND

Cerebral malaria is a major cause of global morbidity and mortality, typically characterized by loss of blood brain barrier integrity and neurological impairment, followed by death in 15-30% cases despite treatment. Cerebral malaria in humans is caused by *Plasmodium falciparum*. The typical symptoms of cerebral malaria include fever, headache and myalgia followed by drowsiness, confusion, impaired balance or coordination, motor impairment, coma and death. Treatment options are currently limited to quinine or artemisinin derivatives, which control parasitemia but are not as effective in reducing mortality. Accordingly, an unmet need exists in the art for effective therapeutic and preventive approaches without adverse side-effects that prevent or treat cerebral malaria.

BRIEF SUMMARY OF THE INVENTION

According to one aspect of the present invention, methods are provided for treating, preventing or ameliorating at least one symptom, indication or complication of cerebral malaria (including, e.g., experimental cerebral malaria, *falciparum* malaria, etc.) in a subject. The methods according to this aspect of the invention comprise administering a therapeutically effective amount of a pharmaceutical composition comprising an angiopoietin or modified angiopoietin protein or a fragment thereof to a subject in need thereof.

In certain embodiments, the at least one symptom, indication or complication is selected from the group consisting of fever, headache and myalgia followed by drowsiness, confusion, vascular leakage, loss of blood-brain barrier integrity, elevated blood level of an endothelial marker, sequestration of parasitized erythrocytes in the brain, impaired balance or coordination, motor impairment, splenomegaly, loss of reflexes and self-preservation, lack of hygiene-related behavior, acute lung injury, convulsion, coma and death. In certain embodiments, the endothelial marker is selected from the group consisting of angiopoietin-1 (Ang1), angiopoietin-2 (Ang2), angiopoietin receptor Tie2, von Willebrand Factor (vWF), intercellular adhesion molecule-1 (ICAM-1), IP-10, E-selectin and vascular cell adhesion molecule-1 (VCAM-1).

According to another aspect of the present invention, methods are provided for improving or increasing survival of a subject following *Plasmodium* infection. The methods comprise administering a therapeutically effective amount of a pharmaceutical composition comprising an angiopoietin or modified angiopoietin protein or a fragment thereof to the subject in need thereof. In a related aspect, the invention provides methods for preventing vascular leakage or protecting blood brain barrier integrity, the method comprising administering a pharmaceutical composition comprising a therapeutically effective amount of an modified angiopoietin protein or a fragment thereof to a subject in need thereof.

In another aspect, the invention provides for methods for preventing severe cerebral malaria in a subject infected with *Plasmodium* spp., the method comprising selecting a subject with more than 0.1% parasitemia; and administering a pharmaceutical composition comprising a therapeutically effective amount of an modified angiopoietin protein or a fragment thereof to the subject in need thereof.

In certain embodiments, the administration of the modified angiopoietin to a subject in need thereof prevents at least one indication of neurological impairment selected from the group consisting of impaired balance or coordination, motor impairment, loss of reflexes and self-preservation, long term neurocognitive injury and impairment including memory deficits and affective disorders, lack of hygiene-related behavior, convulsion, and fitting or seizures.

In certain embodiments, the modified angiopoietin is administered in combination with a second therapeutic agent or therapy. In certain embodiments, the modified angiopoietin is administered as adjunctive therapy along with a second therapeutic agent such as e.g., artesunate.

Exemplary angiopoietin molecules that can be used in the context of the methods of the present invention include, e.g., angiopoietin-1, recombinant angiopoietin (e.g., angiopoietin-1 expressed in adenoviral vector), and a modified angiopoietin (e.g., a fusion protein comprising an angiopoietin or a fragment thereof). According to certain embodiments, the modified angiopoietin is a fusion protein consisting of the fibrinogen-like domain of angiopoietin fused to the Fc fragment of human IgG1 and then forced into a tetramer (Davis et al 2003, Nat. Struct. Biol. 10: 38-44). In certain embodiments, the modified angiopoietin comprises a fusion protein comprising a first fibrinogen-like domain of angiopoietin fused at its C-terminal end to the N-terminal end of an Fc fragment and the Fc fragment fused at its C-terminal end to the N-terminal end of a second fibrinogen-like domain of angiopoietin.

One such type of modified angiopoietin that can be used in the context of the methods of the present invention is AngF1-Fc-F1 (SEQ ID NO: 2).

In certain embodiments, the present invention provides use of an angiopoietin or a modified angiopoietin protein or a fragment thereof of the invention in the manufacture of a medicament to treat or inhibit or prevent cerebral malaria in a subject, including humans.

In another aspect, the present invention includes methods for treating, preventing or ameliorating at least one symptom, indication or complication of cerebral malaria (including, e.g., experimental cerebral malaria, *falciparum* malaria, etc.) in a subject. The methods according to this aspect of the invention comprise administering a therapeutically effective amount of a pharmaceutical composition comprising an anti-Tie2 antibody or an antigen-binding fragment thereof to a subject in need thereof. In certain embodiments, the anti-Tie2 antibody is an activating or agonist antibody.

Other embodiments of the present invention will become apparent from a review of the ensuing detailed description.

BRIEF DESCRIPTION OF THE FIGURES

FIG. 6(a) RMCBS (%) and serum Ang-1 levels (ng/ml) *$p<0.05$ compared to naïve, One-way ANOVA. FIG. 6(b) depicts scatter plots showing linear regression analysis between serum Ang1 (ng/ml) levels and time to death (hours) (Spearman correlation, r value, $p<0.0001$).

FIG. 16(a) shows levels of Evans Blue dye extracted from the brains of C57BI/6 mice infected with PbA and treated with Fc control (A), anti-Ang2 antibody (B), AngF1-Fc-F1 (C), or anti-Ang1/Ang2 comparator antibody (D). FIG. 16(b) shows the percent parasitemia in C57BI/6 mice infected with PbA and treated with Fc control (A), anti-Ang2 antibody (B), AngF1-Fc-F1 (C), or anti-Ang1/Ang2 "comparator" antibody (D).

FIG. 17(a) shows the percent change in RMCBS on Day 6 post PbA infection in C57BI/6 mice treated with AngF1-Fc-F1 or isotype control. FIG. 17(b) shows the percent change over 7 days in RMCBS in C57BI/6 mice infected with PbA and treated with AngF1-Fc-F1 or isotype control.

FIG. 18(a) shows percent parasitemia in C57BI/6 mice infected with PbA and treated with AngF1-Fc-F1 or isotype control. FIG. 18(b) shows the percent fold change in weight of C57BI/6 mice infected with PbA and treated with AngF1-Fc-F1 or isotype control.

FIG. 19 shows plasma protein levels of cytokines TNFα and IFNγ (a), vWF (b), E-selectin, sICAM and VCAM-1 (c) of naïve C57BI/6 mice and mice infected with PbA and treated with AngF1-Fc-F1 or Fc control.

FIG. 21(a) shows percent parasitemia in C57BI/6 mice infected with PbA and treated with artesunate+AngF1-Fc-F1 or artesunate+saline. FIG. 21(b) shows the percent fold change in weight of C57BI/6 mice infected with PbA and treated with artesunate+AngF1-Fc-F1 or artesunate+saline.

DETAILED DESCRIPTION

Figure 1:
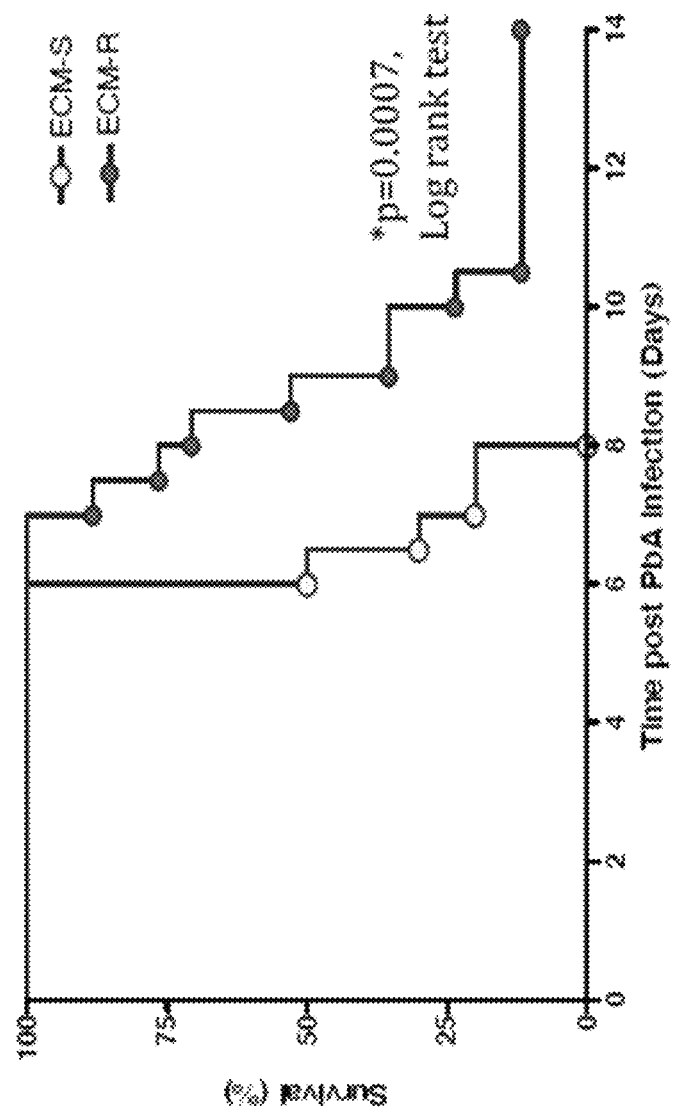
FIG. 1 shows the survival curves of C57BI/6 (Experimental Cerebral Malaria-Susceptible; ECM-S) and BALB/c (Experimental Cerebral Malaria-Resistant; ECM-R) mice infected with *Plasmodium berghei* ANKA (PbA).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating, Preventing or Ameliorating Cerebral Malaria

Cerebral malaria pathogenesis is associated with endothelial activation and loss of blood brain barrier integrity. The angiopoietin-Tie2 signaling pathway is a key regulator of endothelial function. Alterations in the angiogenic balance, specifically increased angiopoietin-2 (Ang2) relative to Ang1, has been associated with poor clinical outcome in cerebral malaria (Yeo et al, 2008 PNAS; Lovegrove et al PLoS ONE 2009; Erdman et al PLoS ONE 2011; Conroy et al PLoS ONE 2011). However, it is unclear whether the Ang-Tie2 pathway is causally involved in cerebral malaria pathogenesis. The inventors have hypothesized that dysregulation in angiopoietins contributes to cerebral malaria pathogenesis, and therefore, interventions to maintain Tie2 activation may promote endothelial stability, prevent deleterious effects to the blood brain barrier and improve outcome following *Plasmodium* infection. Accordingly, it is shown herein, that modified angiopoietins, when administered to an infected subject, protect the blood brain barrier integrity and prevent neurological impairment and death. As disclosed elsewhere herein, the inventors have used a well-known murine model of *Plasmodium berghei* ANKA (PbA)—induced experimental cerebral malaria (ECM) to study alterations in angiopoietins associated with disease severity and fatality and to show that dysregulation of the Ang/Tie2 axis is associated with disease severity and fatality. As shown herein, Ang1 levels inversely correlated with morbidity and mortality in the mouse model of cerebral malaria. Based on the studies shown herein, it is established that Ang1 is necessary to maintain blood brain barrier integrity in response to a lethal malaria challenge and can improve survival above that achieved by conventional treatment (e.g., artesunate) alone. Further, administration of a modified angiopoietin enhanced blood brain barrier integrity and promoted maintenance of a quiescent endothelium via down-regulation of pro-adhesive molecules implicated in parasite sequestration and cerebral malaria pathogenesis.

Accordingly, the present invention includes methods for treating, preventing, or ameliorating at least one symptom, indication or complication of cerebral malaria (including, for example, experimental cerebral malaria, *falciparum* malaria, etc.) in a subject. The methods according to this aspect of the invention comprise administering a therapeutically effective amount of a pharmaceutical composition comprising a modified angiopoietin protein or a fragment thereof to the subject in need thereof.

"Cerebral malaria" (CM), as used herein, means an infectious disease caused by *Plasmodium* species and characterized by loss of blood brain barrier integrity and neurological impairment. The symptoms of CM include, but are not limited to, fever, headache and myalgia followed by drowsiness, confusion, vascular leakage, loss of blood-brain barrier integrity, elevated blood level of an endothelial marker, sequestration of parasitized erythrocytes in the brain, impaired balance or coordination, motor impairment, splenomegaly, loss of reflexes and self-preservation, lack of hygiene-related behavior, acute lung injury, convulsion, fitting, coma and death. The clinicopathology of CM is characterized by sequestration of infected red blood cells in the venules and capillaries of the brain followed by endothelial activation. The term "cerebral malaria" includes but is not limited to severe cerebral malaria caused in humans by *Plasmodium falciparum*, and experimental cerebral malaria (ECM), caused in mice by *Plasmodium berghei* ANKA.

As used herein, the terms "treat", "treating", or the like, mean to alleviate a symptom or a complication, eliminate the causation of a symptom or a complication either on a temporary or permanent basis, or to prevent or slow the appearance of a symptom or complication of cerebral malaria in the subject. In the context of the present invention, the terms "treat", "treating", or the like, refer to reducing or decreasing mortality in a subject infected with *Plasmodium* species. The terms also refer to preventing the loss of blood brain barrier integrity and neurological impairment in a subject with cerebral malaria. In certain embodiments, the present methods are useful for treating or ameliorating at least one symptom, indication or complication of cerebral malaria including, but not limited to, fever, headache and myalgia followed by drowsiness, confusion, vascular leakage, loss of blood-brain barrier integrity, elevated blood level of an endothelial marker, sequestration of parasitized erythrocytes in the brain, impaired balance or coordination, motor impairment, splenomegaly, loss of reflexes and self-preservation, lack of hygiene-related behavior, acute lung injury, convulsion, fitting, coma and death.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, that exhibits one or more symptoms, indications or complications of cerebral malaria, and/or who has been diagnosed with cerebral malaria (CM) and/or in need of amelioration, prevention and/or treatment of cerebral malaria. The term "a subject in need thereof" may also include, e.g., subjects who, prior to treatment, exhibit (or have exhibited) one or more symptoms or indications of cerebral malaria such as, e.g., fever, headache and myalgia followed by drowsiness, confusion, vascular leakage, loss of blood-brain barrier integrity, elevated blood level of an endothelial marker, sequestration of parasitized erythrocytes in the brain, impaired balance or coordination, motor impairment, splenomegaly, loss of reflexes and self-preservation, lack of hygiene-related behavior, acute lung injury, convulsion, fitting, coma and death.

In the context of the present invention, "a subject in need thereof" may include a subset of population, which may show an elevated level of an endothelial marker. Such a subject population may show an elevated level of an endothelial marker such as, e.g., Ang1, Ang2, Tie2, vWF, ICAM-1, E-selectin and VCAM-1.

The methods of the present invention may be used to treat cerebral malaria in adults, including the elderly. In some embodiments, the methods of the present invention are used to treat adults more than 50 years, more than 55 years, more than 60 years, more than 65 years, or more than 70 years old.

In some embodiments, the methods herein may be used to treat cerebral malaria in children who are 3 years old. For example, the present methods may be used to treat infants who are less than 1 month, 2 months, 3 months, 4 months, 5 months, 6 months, 7 months, 8 months, 9 months, 10 months, 11 months or less than 12 months old. In other embodiments, the methods of the present invention may be used to treat children who are more than 3 years old, more than 4 years, 5 years, 6 years, 7 years, 8 years, 9 years, 10 years, 11 years, 12 years, 13 years, 14 years, or more than 15 years old.

The present invention also includes methods for increasing survival in a subject with cerebral malaria. The methods according to this aspect of the invention comprise administering to the subject one or more doses of a pharmaceutical composition comprising a modified angiopoietin to increase survival in the subject.

The present invention also includes methods to prevent severe cerebral malaria in a subject infected with *Plasmodium* species, the methods comprising administering a therapeutically effective amount of a pharmaceutical composition comprising a modified angiopoietin to the subject in need thereof. In certain embodiments, the modified angiopoietin is administered as an exogenous protein.

The term "preventing" as used herein refers to preventing development of disease. The term, as used herein, also includes preventing vascular leakage, protecting blood brain barrier integrity and the onset of neurological symptoms such as seizures and paralysis upon infection with the pathogen. In some embodiments, the term refers to preventing endothelial dysfunction, which is a key pathological feature of cerebral malaria (including experimental cerebral malaria).

The present invention includes methods for treating, preventing or reducing the severity of cerebral malaria comprising administering a therapeutically effective amount of a pharmaceutical composition comprising a modified angiopoietin to a subject in need thereof, wherein the pharmaceutical composition is administered to the subject in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In some embodiments, the therapeutic dosing regimen comprises administering multiple doses of the pharmaceutical composition to the subject at a frequency of about once a day, about 2 times a day, about 3 times a day or more than 4 times a day.

In certain embodiments, the modified angiopoietin is administered subcutaneously, intravenously, intracranially, intraventricularly, or delivered systemically in an adenoviral vector to a subject in need thereof.

The methods of the present invention, according to certain embodiments, comprise administering to a subject a therapeutically effective amount of a pharmaceutical composition comprising a modified angiopoietin in combination with a second therapeutic agent. The second therapeutic agent may be an agent selected from the group consisting of an artemisinin, quinine, or a variant or derivative thereof (e.g., artesunate), a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab)], an activating anti-Tie2 antibody, an Ang2 antagonist, an antihistamine, and a non-steroidal anti-inflammatory drug (NSAID). As used herein, the phrase 'in combination with" means that the pharmaceutical composition comprising a modified angiopoietin is administered to the subject at the same time as, just before, or just after administration of the second therapeutic agent. In certain embodiments, the second therapeutic agent is administered as a co-formulation with the modified angiopoietin.

The present invention also includes methods for treating, preventing or ameliorating at least one symptom, indication or complication of cerebral malaria in a subject, wherein the methods comprise administering a therapeutically effective amount of a pharmaceutical composition comprising an anti-Tie2 antibody or an antigen-binding fragment thereof to the subject in need thereof. In certain embodiments, the anti-Tie2 antibody is an activating or agonist antibody, e.g., the antibody upon binding to Tie2 increases the activity of Tie2 or otherwise stimulates Tie2 signaling. In certain embodiments, the anti-Tie2 antibody is an antibody as set forth in US20130209492. The anti-Tie2 antibody may be administered subcutaneously, intravenously, or intracranially at a dosage of from about 0.1 mg/kg to about 100 mg/kg of the subject's body weight. In certain embodiments, the activating anti-Tie2 antibody is administered in combination with a second activating anti-Tie2 antibody to the subject in need thereof.

In another aspect, the present invention includes methods for treating, preventing or ameliorating at least one symptom, indication or complication of a disease or disorder associated with dysfunction of the Ang-Tie2 pathway in a subject. The methods comprise administering a therapeutically effective amount of a pharmaceutical composition comprising a modified angiopoietin protein or a fragment thereof to the subject in need thereof. In certain embodiments, the angiopoietin or variants thereof may be used to treat, prevent or ameliorate at least one symptom or indication of a disease or disorder including cerebral malaria, sepsis, anthrax, dengue, hemorrhagic fever (including viral hemorrhagic fever, e.g., lassa fever, Yellow fever, and Ebola fever), toxic shock syndrome, HUS, hemorrhagic shock (model for massive blood loss due to traumatic injury, e.g., IED), ischemic reperfusion, hemolytic uremic syndrome, myocardial infarction and stroke.

Modified Angiopoietins

The methods of the present invention comprise administering to a subject in need thereof a therapeutic composition comprising an angiopoietin or a variant thereof. As used herein, an "angiopoietin" includes angiopoietin-1 (Ang1) or angiopoietin-2 (Ang2).

Non-limiting examples of categories of modified angiopoietins include recombinant angiopoietins (e.g., angiopoietin expressed in an adenoviral vector; Thurston et al 2000, Nat. Med.), mutant and chimeric forms of angiopoietins, and fusion proteins comprising angiopoietin or a fragment thereof that specifically bind Tie1 and/or Tie2 receptors.

According to certain exemplary embodiments of the present invention, the modified angiopoietin is a fusion protein comprising one or more domains of the angiopoietin molecule fused to a multimerizing domain. In general terms, the multimerizing domain(s) of the present invention function to connect the various components of the angiopoietin molecule (e.g., the fibrinogen-like domains) with one another. As used herein, a "multimerizing domain" is any macromolecule that has the ability to associate (covalently or non-covalently) with a second macromolecule of the same or similar structure or constitution. For example, a multimerizing domain may be a polypeptide comprising an immunoglobulin $C_H3$ domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group. In certain embodiments, the multimerizing domain is an Fc fragment or an amino acid sequence of 1 to about 200 amino acids in length containing at least one cysteine residues. In other embodiments, the multimerizing domain is a cysteine residue or a short cysteine-containing peptide. Other multimerizing domains include peptides or polypeptides comprising or consisting of a leucine zipper, a helix-loop motif, or a coiled-coil motif.

In certain embodiments, the modified angiopoietin is a fusion protein comprising one or more fibrinogen-like domains of the angiopoietin-1 molecule fused to the Fc fragment of an immunoglobulin comprising any of the amino acid sequences, as set forth in U.S. Pat. No. 7,008,781. In certain exemplary embodiments, the fusion protein that can be used in the context of the methods of the present invention comprises a first fibrinogen-like domain of angiopoietin fused at its C-terminal end to the N-terminal end of an IgG Fc fragment and the C-terminal of the Fc fragment fused to the N-terminal end of a second fibrinogen-like domain of angiopoietin (Davis et al, Nat. Struct. Biol. 2003), wherein the angiopoietin may be Ang1 or Ang2.

According to certain exemplary embodiments, the methods of the present invention comprise the use of the modified angiopoietin referred to and known in the art as AngF1-Fc-F1. In certain embodiments, the modified angiopoietin is a dimer comprising two AngF1-Fc-F1s that associate through intramolecular association of the Fc fragments (also referred to as BowAng1, as disclosed in Davis et al, Nat. Struct. Biol. 2003). According to certain embodiments, the fusion protein comprises the amino acid sequence of SEQ ID NO: 2. In some embodiments, the fusion protein comprises the amino acid sequence of SEQ ID NO: 4.

Other modified angiopoietins that can be used in the context of the methods of the present invention include any of the modified angiopoietin molecules as set forth in U.S. Pat. Nos. 6,265,564, 6,441,137, and 6,825,008.

In certain embodiments, the angiopoietin or variants thereof may be used to treat, prevent or ameliorate at least one symptom or indication of a disease or disorder including sepsis, dengue, hemorrhagic fever (including viral hemorrhagic fever, e.g., lassa fever, Yellow fever, and Ebola fever), toxic shock syndrome, HUS, hemorrhagic shock (model for massive blood loss due to traumatic injury, e.g., IED), ischemic repurfusion, hemolytic uremic syndrome, myocardial infarction and stroke.

Pharmaceutical Compositions

The present invention includes methods which comprise administering a modified angiopoietin to a subject wherein the modified angiopoietin is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of the modified angiopoietin (e.g., AngF1-Fc-F1) administered to a subject according to the methods of the present invention is, generally, a therapeutically effective amount. As used herein, the phrase "therapeutically effective amount" means an amount of modified angiopoietin that results in one or more of: (a) a reduction in the severity or duration of a symptom, indication or complication of severe cerebral malaria; (b) increased survival; (c) protection of the blood brain barrier integrity; and (d) prevention of neurological impairment in the subject.

In the case of a modified angiopoietin, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the modified angiopoietin.

The amount of the modified angiopoietin contained within the individual doses may be expressed in terms of milligrams of protein per kilogram of the subject's body weight (i.e., mg/kg). For example, the modified angiopoietin may be administered to a subject at a dose of about 0.0001 to about 100 mg/kg of patient body weight. In certain embodiments, the modified angiopoietin is administered to a subject in need thereof at a dose of about 5-25 mg/kg of the subject's body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Alterations in Endothelial Regulators in the Murine *Plasmodium berghei* ANKA (Pba)-Induced Model of Experimental Cerebral Malaria (ECM)

In this Example, the alterations in endothelial regulators in *Plasmodium berghei* ANKA (PbA)-induced experimental cerebral malaria in a mouse model were studied. This model is based on the observation that C57Bl/6 mice are susceptible to the murine parasite *P. berghei* ANKA which produces a severe, ultimately fatal disease with neurological symptoms paralleling the symptoms and disease development of cerebral malaria in humans infected with *Plasmodium falciparum*. In contrast to C57Bl/6 mice, BALB/c mice are resistant to PbA, in that they do not develop encephalopathy, although they become infected and achieve similar or sometimes higher levels of parasite density. This study showed that dysregulation of the Ang/Tie2 axis was associated with disease severity and fatality. Further, Ang1 levels inversely correlated with morbidity and mortality in the mouse model of cerebral malaria.

Materials and Methods

PbA-Induced ECM Model: Infection
Cryopreserved *Plasmodium berghei* ANKA (PbA; MR4, Manassas, Va.) was passaged through naïve C57Bl/6 mice. For the experiment, infection was initiated in C57Bl/6 and BALB/c mice by intraperitoneal (ip) injection of 1×10$^6$ freshly-isolated parasitized erythrocytes (PE) obtained from donor passage mice. Parasitemia was monitored by thin-blood smear stained with modified Geimsa stain (Protocol Hema3 Stain Set, Sigma, Oakville, ON) by counting at least 1500 erythrocytes. The infected mice were monitored for survival, neurological impairment, vascular leakage, parasite burden, and levels of angiogenic factors and markers of endothelial activation.

Survival and Assessment of Health Status
Post-infection survival of mice was plotted as Kaplan Meier curves using a log rank test for comparison. Quantitative assessment of ECM-associated neurological impairment (impaired coordination and motor performance) was performed daily using the 10 parameter Rapid Murine Coma and Behavioral Score (RMCBS), as previously described by Carroll R W, et al. 2010 in PLoS ONE 5: e13124. Signs of ECM include impaired balance/coordination, motor impairment (ataxia, hemiplegia/paraplegia), loss of reflexes and self-preservation, lack of hygiene-related behavior (grooming) and/or fitting. For each parameter, a score was assigned from 0 to 2, with 0 indicating the lowest function and a score of 2 the highest. Total scores for each mouse were calculated and provided as a percentage of the total possible score. Mice with a score of 35% or less were deemed to have severe ECM.

Evans Blue Permeability Assay
Vascular permeability in the brain was assessed using Evans blue (EB) dye. Mice were intravenously injected via tail vein with 0.1 mL of 1% Evans blue dye solution (Evans Blue powder; Sigma-Aldrich in PBS, filter sterilized) when clinical signs of ECM were observed. Mice were euthanized with isoflurane (99.9% inhalational anesthetic) after 1 hour, perfused with 50 mL of PBS (1×). Brains were dissected aseptically, weighed, photographed and placed in 1 mL N, N-dimethylformamide for 48 hours at room temperature to extract dye from tissue. Absorbance was measured at 620 nm. The concentration was calculated using a standard curve of EB dye and expressed as ng dye per gram of brain tissue.

Detection of Cytokine Markers of Endothelial Activation
Peripheral whole blood was collected by saphenous venipuncture on day 0 (d 0; prior to PbA infection) and d 6 p.i. into heparinized tubes (Starstedt). Plasma was isolated from whole blood samples by centrifugation at 1000×g for 15 min. Plasma samples were aliquoted and stored at −80° C. until analyzed. Levels of mouse intercellular adhesion molecule-1 (sICAM-1/CD54), E-Selectin (sE-Sel/CD62E) and Vascular Cell Adhesion Molecule-1 (sVCAM-1/CD106) in their soluble forms were determined in plasma using commercially available murine ELISA kits (R&D Systems, Minneapolis, USA), according to the manufacturers protocol. Levels of von Willebrand Factor antigen (vWF:Ag) was measured in serum by ELISA as follows: 96-well MaxiSorp plates (Nunc) were coated overnight at 4° C. with a polyclonal antibody anti-human vWF (1:600, Dako, Glostrup, Denmark) in 0.01M PBS. Mouse serum was plated in 1% BSA-PBS and bound vWF:Ag was detected with horseradish peroxidase (HRP)-conjugated polyclonal antibody anti-human vWF (1:8000, Dako). Plates were developed with a 3,3',5,5'-tetramethylbenzidine (TMB) substrate solution and the absorbance was read at 450 nm, after the colorimetric reaction was stopped with $H_2SO_4$. vWF:Ag concentration was interpolated from a standard curve created with human vWF of a known concentration from fresh frozen plasma (1:500, American Diagnostica, Stamford, Conn.) that was included on each plate. IFN-gamma and TNF-alpha were determined in plasma using commercially available murine ELISA kits (eBioscience), according to the manufacturer's protocol.

Statistical Analysis

Statistical analysis was performed using GraphPad Prism version 4.00 (San Diego, Calif.). Post-infection survival of mice was plotted as Kaplan Meier curves and assessed using log-rank test. Survival studies were conducted in triplicate and data pooled unless otherwise specified. Shapiro-Wilk test was used to determine normally distributed data and comparisons between groups were assessed using the non-parametric Mann-Whitney test or Kruskal-Wallis test followed by Dunn's post-hoc. Two-way ANOVA was used to compare between groups over multiple time-points. For plasma biomarker testing, the Friedman test with Dunn's multiple comparison was used to compare levels between samples collected from patients at different time points (e.g., admission and convalescence). All data are presented as median and IQR (non-parametric), unless otherwise stated. Normally distributed data is presented as mean and SEM. A $p<0.05$ was considered statistically significant. Data from multiple experiments were normalized to the geometric mean of the infected but untreated group of each experiment for comparisons.

Results

As shown in FIG. 1, the resistant BALB/c mice (also referred to as "ECM-R") showed significantly prolonged survival ($p=0.0007$, log rank test) following infection with PbA as compared to the susceptible C57Bl/6 mice (also referred to as "ECM-S"). The resistant BALB/c mice showed 100% survival for 7 days post infection with survival dropping to more than 10% by Day 10 and up to Day 14 (when the mice were sacrificed). In contrast, the susceptible C57Bl/6 mice showed only about 50% survival as early as Day 6 with 0% by Day 8 post infection.

Figure 2:
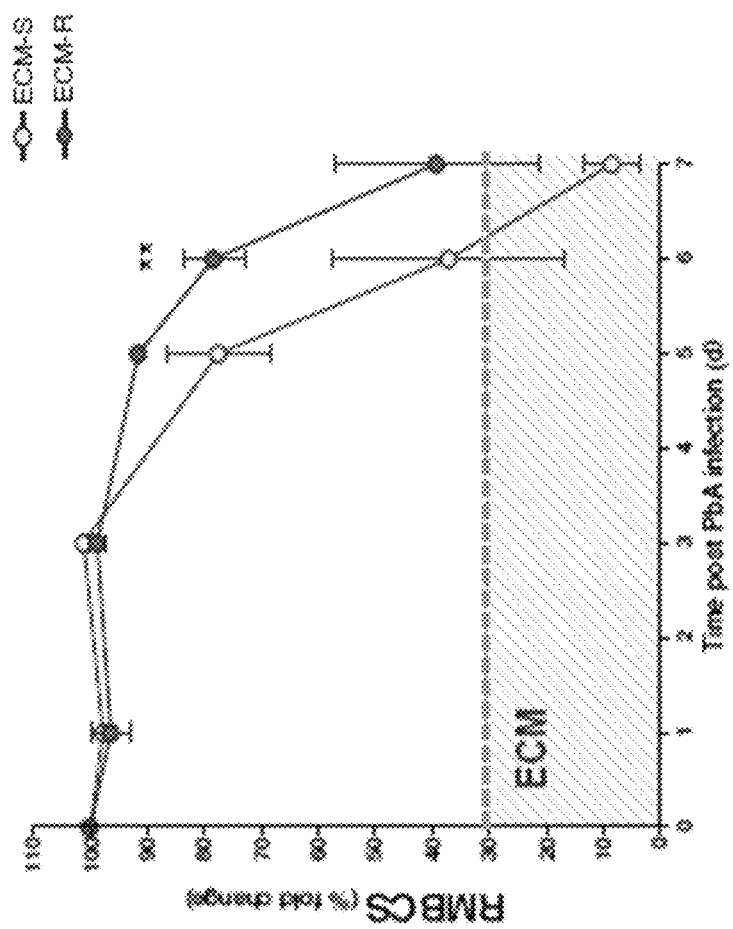
FIG. 2 shows the percent fold change in Rapid Murine Coma and Behavioral Score (RMCBS) in ECM-S and ECM-R mice infected with PbA.
Figure 3:
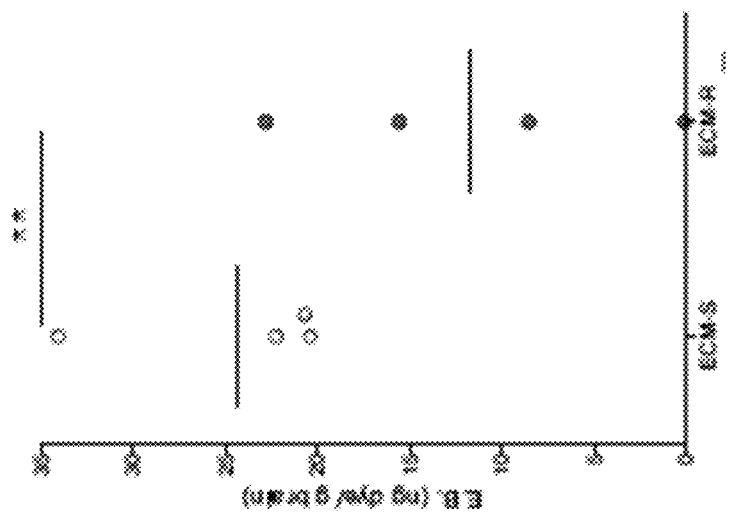
FIG. 3 shows comparative levels of Evans Blue dye extracted from the brains of ECM-R and ECM-S mice infected with PbA.
Figure 4:
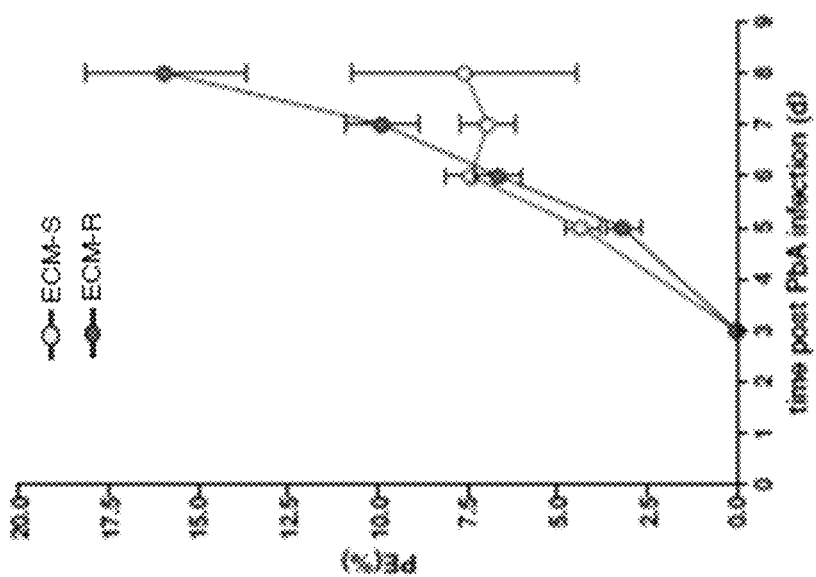
FIG. 4 shows percent parasitemia in ECM-S and ECM-R mice infected with PbA.

The ECM-S mice showed neurological impairment as evidenced by scores less than 35% around Day 6 as compared to the resistant ECM-R mice which showed an absence of neurological impairment (FIG. 2). Evans Blue (EB) extravasation was used to assess vascular permeability and blood-brain-barrier dysfunction. Following perfusion to remove circulating dye, extravasated EB level in brain parenchyma of PbA-infected ECM-S mice was 2-fold higher than level in ECM-R mice with comparable parasite burdens [mean (SD) EB dye/g tissue: 10.7 (7.9) for ECM-R mice vs. 22.9 (7.2) for ECM-S mice; $p=0.005$], consistent with increased vascular leakage and loss of blood-brain-barrier integrity (FIG. 3). This was independent of observed parasitemia as evidenced by a greater parasite burden in the resistant mice as compared to the susceptible mice (FIG. 4).

Figure 5:
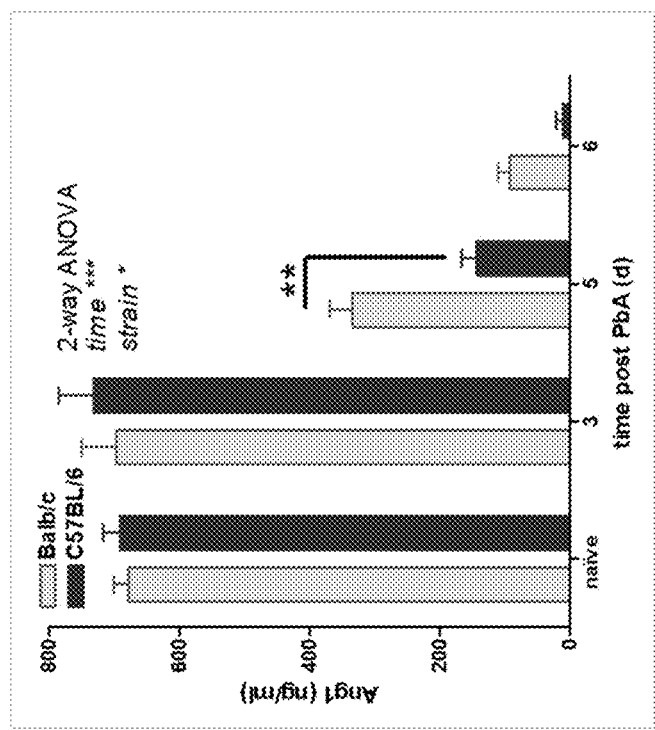
FIG. 5 shows Ang-1 serum levels over the course of PbA infection. ***$p<0.0001$ (time), *$p<0.05$ (strain) and **$p<0.001$ (2-way ANOVA with Bonferroni post-test for the indicated comparison).
Figure 6B:
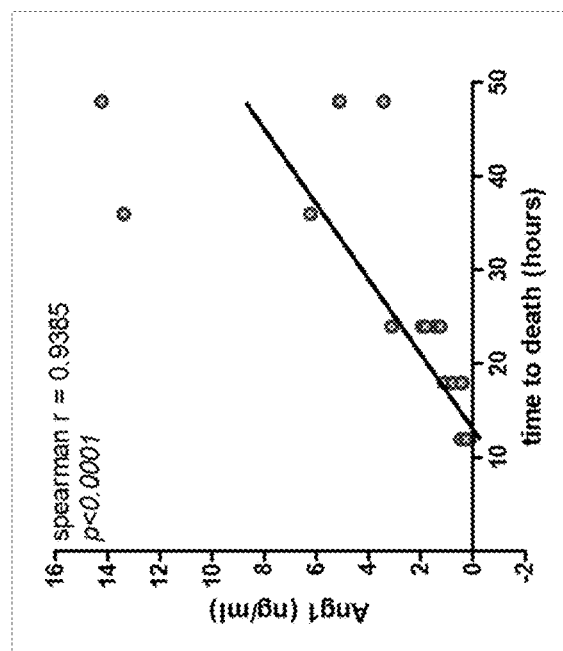
FIGS. 6(a) and 6(b)
Figure 6A:
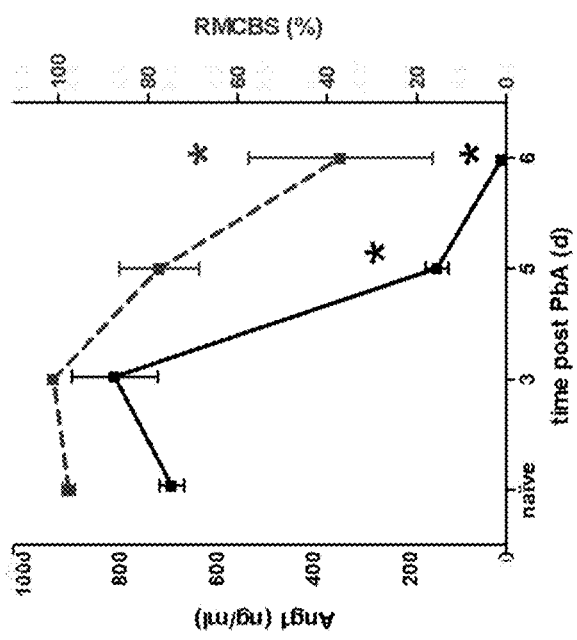

The ECM-R mice differed from the ECM-S mice in the levels of angiogenic factors Ang1, Ang2 and vWF upon PbA infection. Longitudinal evaluation over the course of infection showed that Ang1 levels decreased with time ($p<0.0001$, 2-way ANOVA; FIG. 5). The kinetics of Ang1 decline following infection was significantly different in ECM-R vs. ECM-S mice ($p=0.02$, 2-way ANOVA). During the acute phase of disease, ECM-R mice maintained significantly higher Ang1 levels as compared to ECM-S mice ($p<0.001$). For both strains, the loss of circulating Ang1 was associated with the onset of neurological impairment and ECM as determined by a significant decline in the RMCBS. Ang1 serum levels (ng/ml) correlated significantly with RMCBS (%) scores ($p<0.05$; FIG. 6a) and with time to death (hours) ($p<0.0001$; FIG. 6b). Overall, when assessed on day 6 post-infection, mice with lowest levels of circulating Ang1 were significantly more likely to proceed to a fatal outcome, supporting the hypothesis that Ang1 may be a critical determinant of survival.

Figure 7:
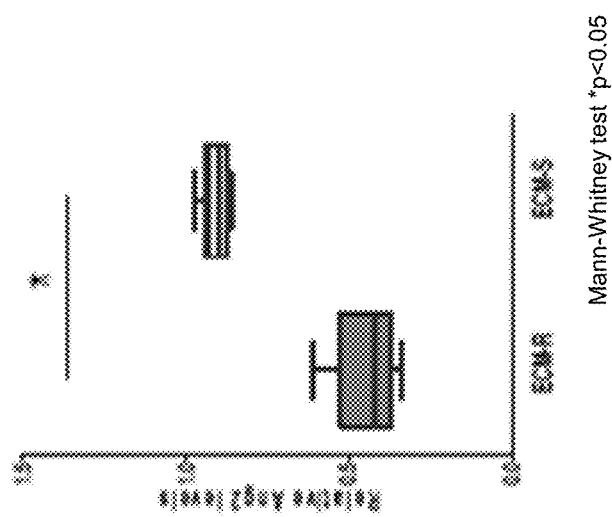
FIG. 7 shows relative Ang2 protein levels in ECM-R and ECM-S mice post PbA infection.
Figure 8:
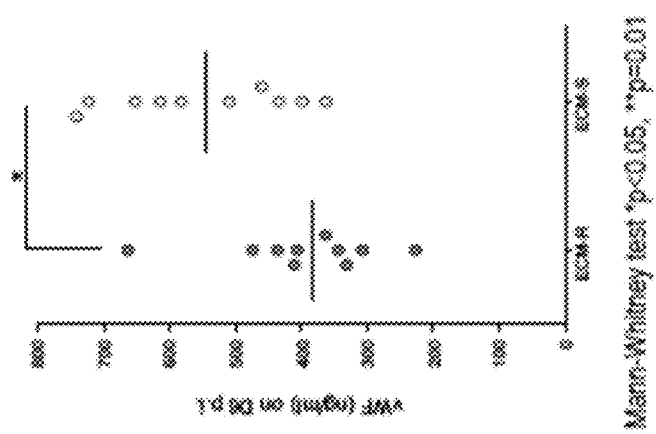
FIG. 8 shows vWF protein levels in ECM-R and ECM-S mice on Day 6 post infection with PbA.
Figure 9:
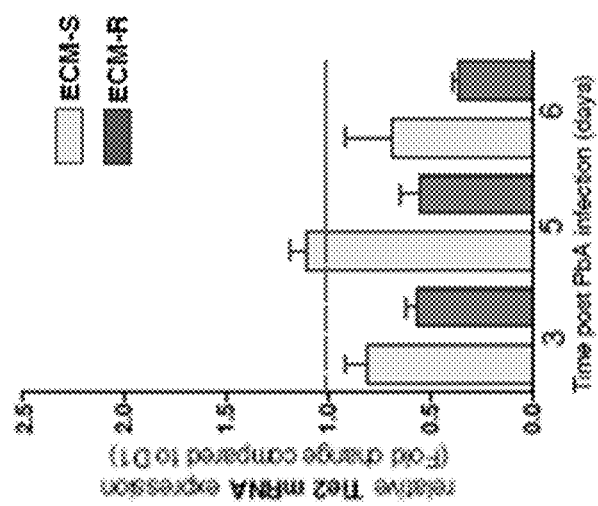
FIG. 9 shows the relative Tie2 mRNA levels in ECM-R and ECM-S mice post PbA infection.

The ECM-R mice showed significantly lower Ang2 and vWF levels (FIGS. 7-9).

Example 2: Blocking Ang2 does not Confer Improved Protection Against the Development of Experimental CM In this Example, the effect of Ang2 blockade on PbA-induced ECM in a mouse model was assessed. Twenty 057Bl/6 mice were infected by *Plasmodium berghei* ANKA (PbA) via an intraperitoneal injection of $1\times10^6$ freshly-isolated parasitized erythrocytes (PE) obtained from donor passage mice on Day 0. The infected mice were treated with 15 mg/kg of an anti-Ang2 antibody, H1H685, as described in US Patent Application Publication No. US20110027286, on Days −1, 1, 4, and 7 post-infection via subcutaneous injection. The mice were monitored for survival, neurological impairment, parasite burden and plasma protein levels, as described in detail in Example 1.

Figure 10:
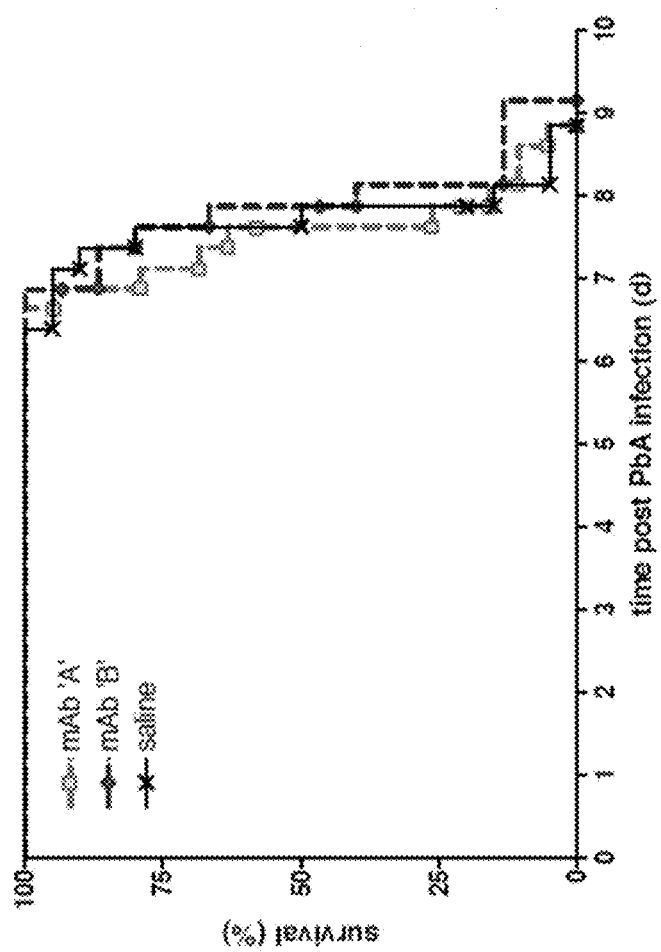
FIG. 10 shows the survival curves of C57BI/6 mice infected with PbA and treated with anti-Ang2 antibody (mAb isotype control (mAb 'A') or saline.
Figure 11:
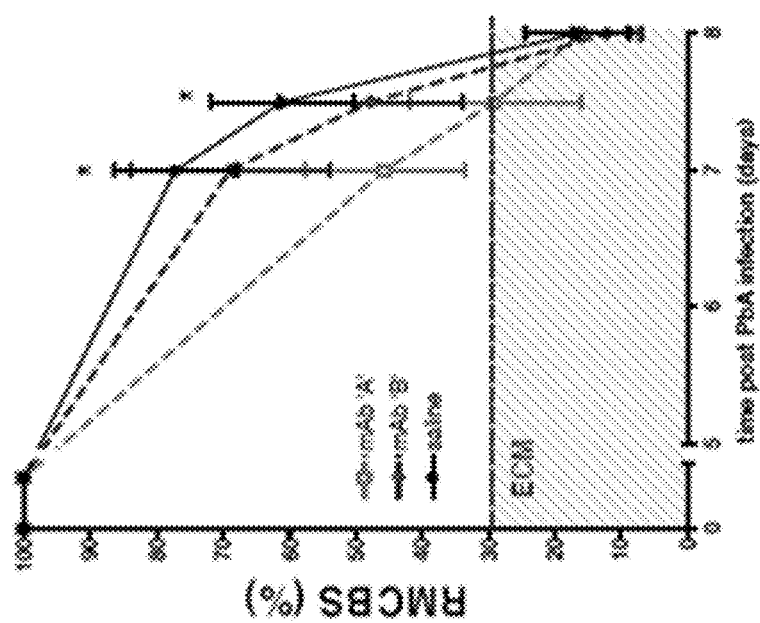
FIG. 11 shows percent fold change in RMCBS in C57BI/6 mice infected with PbA and treated with anti-Ang2 antibody (mAb isotype control (mAb 'A') or saline.
Figure 12:
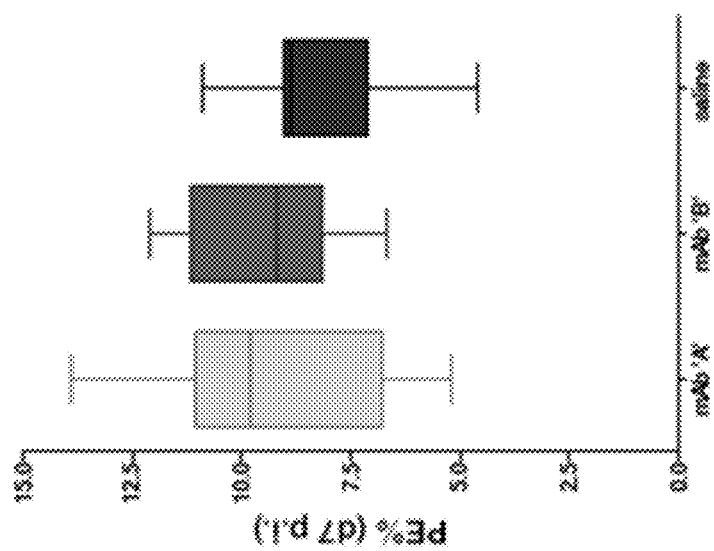
FIG. 12 shows percent parasitemia on Day 7 post PbA infection in C57BI/6 mice treated with anti-Ang2 antibody (mAb isotype control (mAb 'A') or saline.
Figures 13A, 13B:
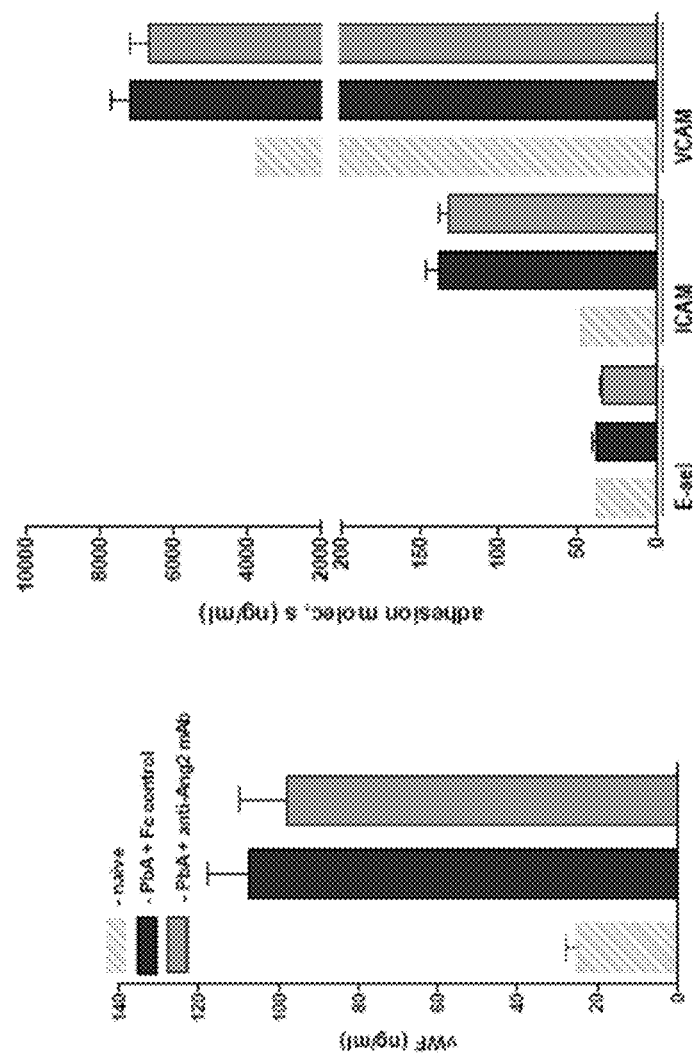
FIGS. 13(a) and 13(b) show the plasma protein levels of (FIG. 13(a)) vWF and (FIG. 13(b)) E-selectin, ICAM and VCAM in naïve C57BI/6 mice (hatched bars) or mice infected with PbA and treated with anti-Ang2 antibody (mAb 'B') (grey bars) or isotype control (mAb 'A') (black bars).

FIG. 10 shows a Kaplan Meier curve plotting the survival of mice infected with PbA and treated with anti-Ang2 antibody (referred to as "mAb 'B'" in FIG. 10), or an isotype control (mAb 'A') or saline. Blocking Ang2 with the anti-Ang2 antibody did not lead to increased survival of infected mice as compared to the isotype control. Treatment with anti-Ang2 antibody also did not prevent neurological impairment in the infected mice (FIG. 11), though there was no significant difference in the parasite burden between infected mice treated with anti-Ang2 antibody, the isotype control or saline (FIG. 12). The plasma protein levels of vWF, ICAM, VCAM and E-selectin did not differ significantly in the mice treated with the anti-Ang2 antibody, or isotype control (FIG. 13).

Example 3: Therapeutic Administration of Ang1 Significantly Improves Survival of Mice Infected with PbA In this Example, the effect of Ang1 administration on PbA-induced ECM in a mouse model was studied. Eighty C57Bl/6 mice were infected by *Plasmodium berghei* ANKA (PbA) via an intraperitoneal injection of $1\times10^6$ freshly-isolated parasitized erythrocytes (PE) obtained from donor passage mice on Day 0. The infected mice were divided into four groups and were treated with either 15 mg/kg of an anti-Ang2 antibody (see Example 2), a "comparator" dual blocking antibody of Ang1/Ang2 or an isotype control, or with 25 mg/kg of AngF1-Fc-F1 (SEQ ID NO: 2) via subcutaneous injection on Day 4 and Day 6 post infection. The "comparator" dual Ang1/Ang2 blocking antibody was the peptibody 2xCon4C (AMG386) as set forth in U.S. Pat. No. 7,205,275 (Amgen). The mice were monitored for survival, neurological impairment, parasite burden, and plasma protein levels, as described in detail in Example 1.

Figure 14:
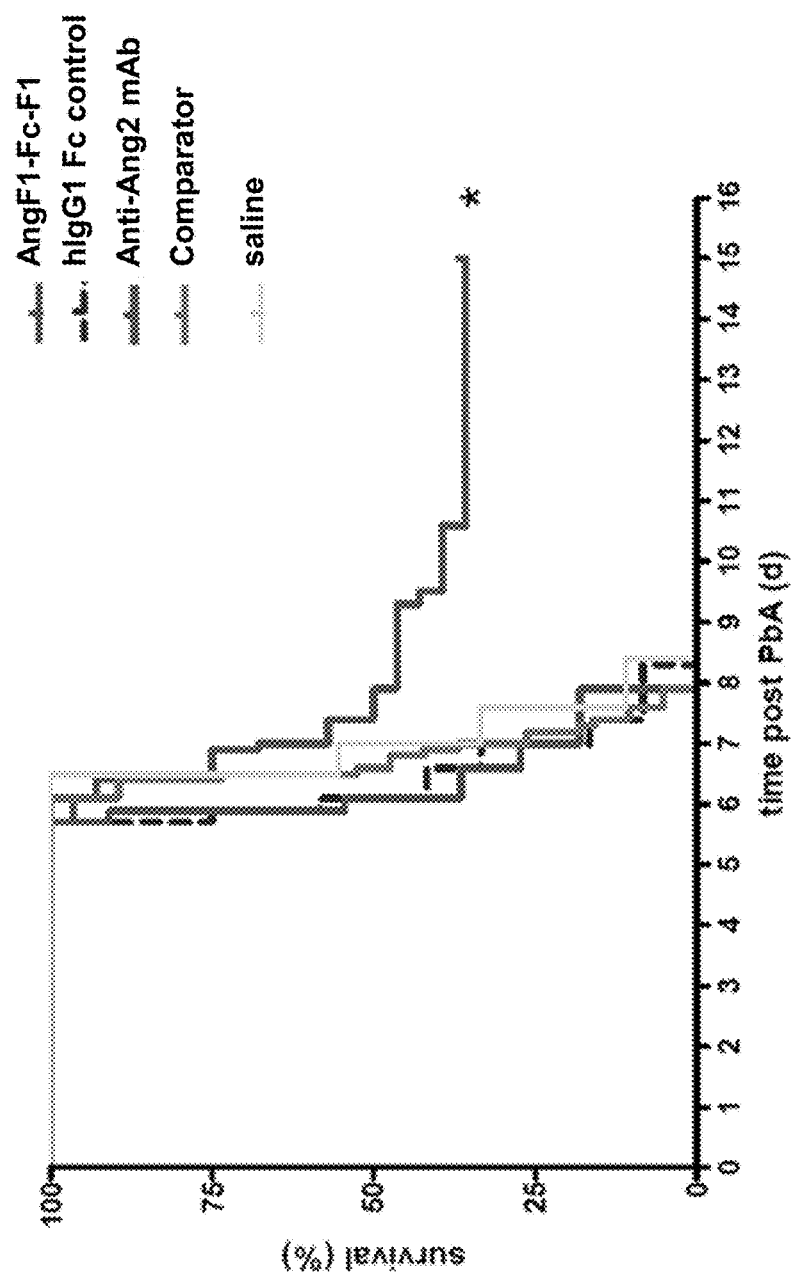
FIG. 14 shows survival curves of C57BI/6 mice infected with PbA and treated with AngF1-Fc-F1, Fc control, anti-Ang2 antibody, a dual Anti-Ang1/Ang2 antibody ("comparator") or saline.
Figure 15:
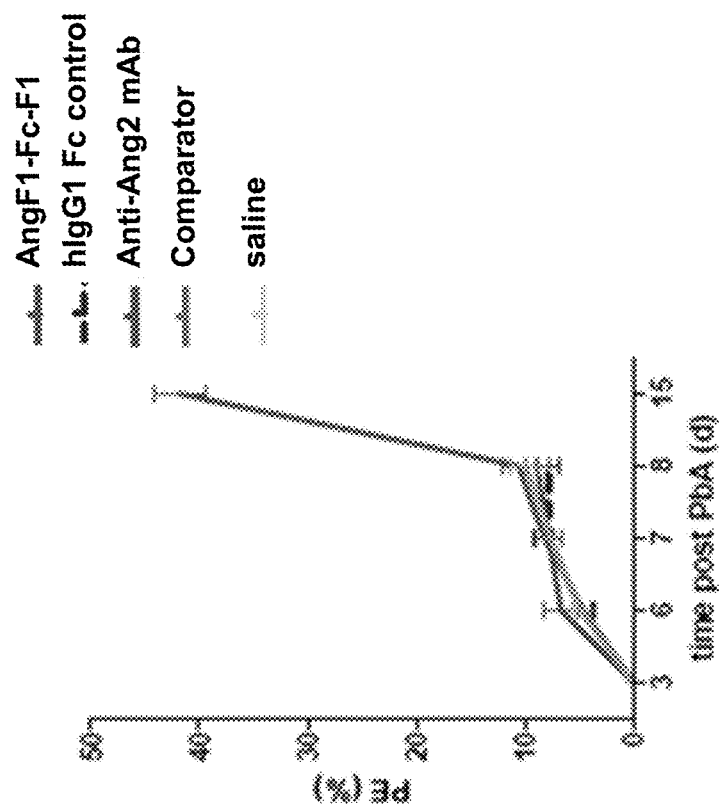
FIG. 15 shows percent parasitemia in C57BI/6 mice infected with PbA and treated with AngF1-Fc-F1, Fc control, anti-Ang2 antibody, a dual Anti-Ang1/Ang2 antibody ("comparator") or saline.
Figure 16B:
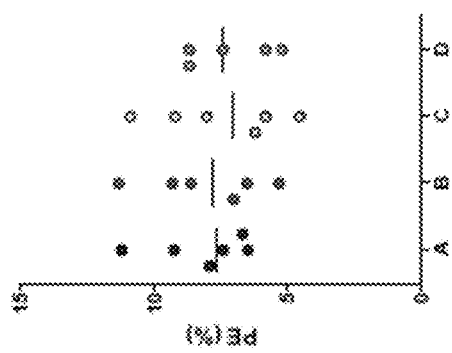
FIGS. 16(a) and 16(b)
Figure 16A:
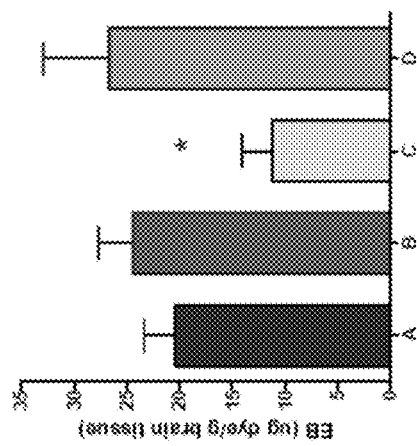

As shown in FIG. 14, therapeutic administration of AngF1-Fc-F1 to mice infected with PbA significantly improved survival ($p<0.05$, log rank test) compared to mice treated with the isotype control, anti-Ang2 antibody or the dual blocking antibody. The mice treated with AngF1-Fc-F1 showed more than 35% survival up to at least Day 15 p.i. as compared to the mice treated with the other three treatments which showed 0% survival by Day 8 post infection, though the percent parasitemia across all treatments was similar (FIG. 15). The treatment with AngF1-Fc-F1 also protected blood brain barrier integrity as shown by Evans Blue dye uptake (FIG. 16). The mice treated with AngF1-Fc-F1 showed significantly low amount of dye uptake (panel C of FIG. 16*a*), consistent with maintenance of an intact blood brain barrier and reduced vascular permeability (p<0.05, Kruskal-Wallis), even though the percent parasitemia was similar (FIG. 16*b*). This confirmed that exogenous Ang1 is sufficient to maintain blood-brain-barrier integrity following a lethal malaria challenge.

Figures 17A, 17B:
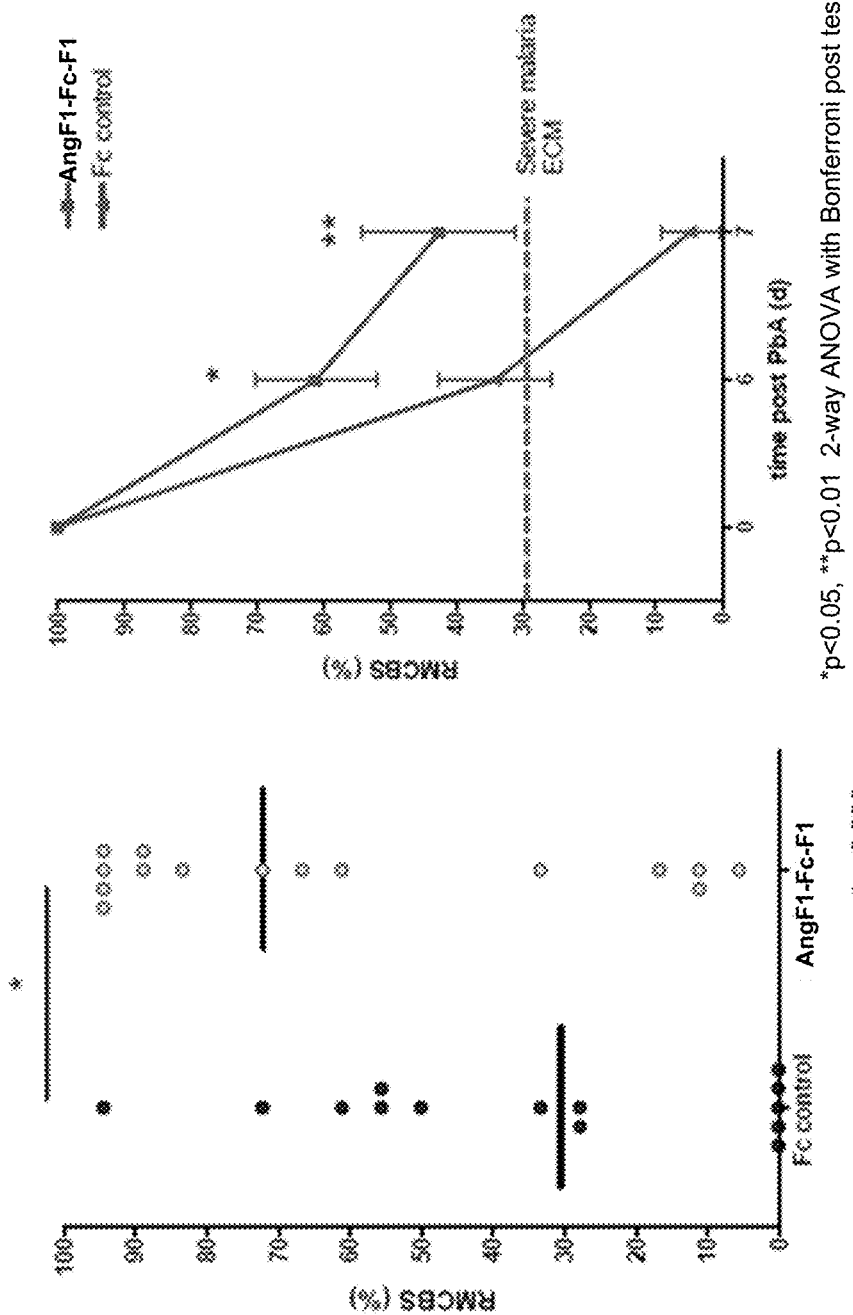
FIGS. 17(a) and 17(b)
Figures 18A, 18B:
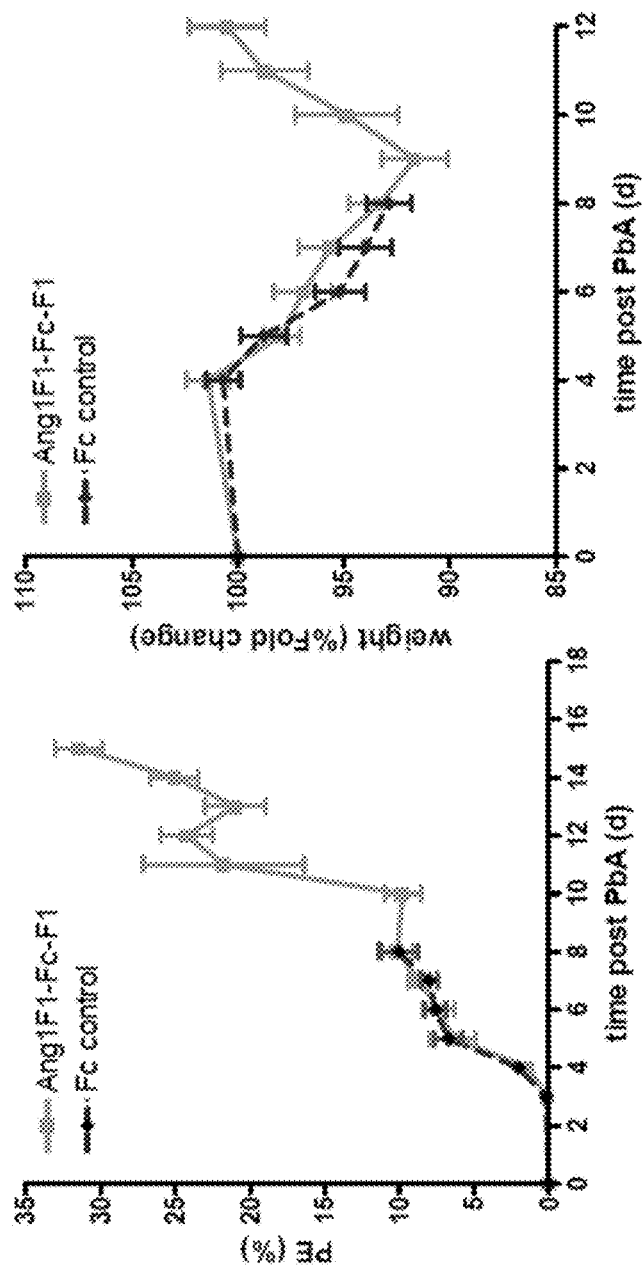
FIGS. 18(a) and 18(b)

The therapeutic administration of AngF1-Fc-F1 also prevented ECM-associated morbidity and neurological impairment (FIG. 17), independent of changes to peripheral parasitemia (FIG. 18). By day 6 post-infection, the majority of control mice had progressed to ECM, whereas disease progression was mitigated in treated mice. Infected AngF1-Fc-F1-treated mice displayed similar weight loss to control-treated mice.

Figures 19A, 19B, 19C:
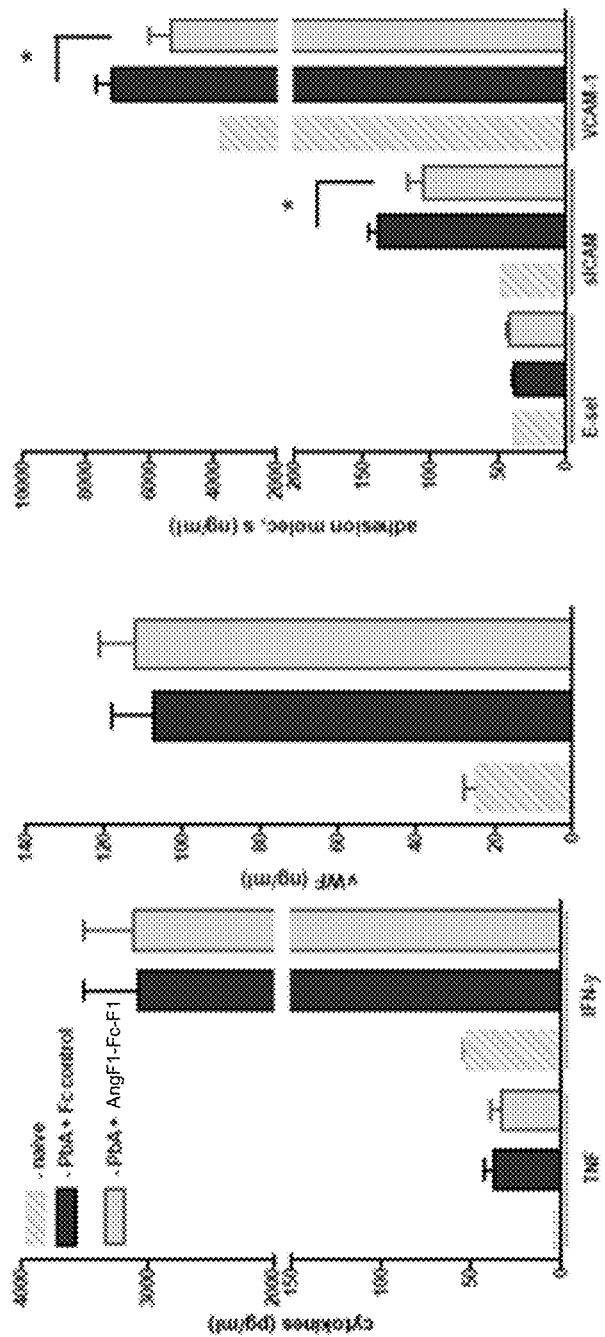
FIGS. 19(a), 19(b) and 19(c)

To determine whether vascular protection with AngF1-Fc-F1 occurred secondary to a reduction in inflammatory cytokines or whether protection was due to a direct enhancement of vascular stability in the face of a systemic inflammatory response, plasma samples from treated and untreated PbA-infected mice were assayed for key pro-inflammatory cytokines. PbA-infected mice showed a significant increase in TNF and IFNγ on day 6 post-infection (3-fold increase in TNF and a 60-fold increase in IFNγ compared to baseline, p<0.01 for both, one-way ANOVA) despite treatment. Treatment with AngF1-Fc-F1 did not affect levels of TNF or IFNγ, with both control and treated mice showing a similar up-regulation in response to infection (FIG. 19*a*).

Pro-inflammatory cytokine stimulation and/or direct endothelial interactions with parasitized erythrocytes may contribute to a number of pathological events implicated in CM, including up-regulation of endothelial cell receptors that mediate parasite cytoadhesion. Disruption of parasite sequestration to host receptors via down-regulation of cell adhesion molecules (CAMs), such as ICAM-1 and/or vascular cellular adhesion molecule-1 (VCAM-1), may lessen microvascular obstruction and endothelial dysfunction. Therefore, the effect of Ang1 treatment on reduction of circulating levels of soluble forms of CAMS, considered as an indicator of endothelial activation and a pro-adhesive vascular phenotype, was investigated. Analysis of plasma samples collected on day 6 post-infection showed a 4-fold increase in circulating levels of sICAM-1 with PbA infection, compared to baseline (p<0.001, One-way ANOVA with Bonferroni test for multiple comparisons; FIG. 19*c*). These levels were significantly reduced with Ang1 treatment compared to PbA-infected controls (p<0.05; FIG. 19*c*). Similarly, sVCAM-1 levels significantly increased at day 6 post-infection with PbA (5-fold increase, p<0.001; FIG. 19*c*) and Ang1 treatment significantly reduced circulating levels of sVCAM-1 compared to PbA-infected controls (p<0.05, FIG. 19*c*). These data indicate that Ang-1-Tie-2 interactions help to maintain vascular quiescence in the face of systemic inflammatory response, in part through preservation of an anti-adhesive vascular phenotype via down regulation of adhesion molecules.

This study showed that therapeutic administration of Ang1 (AngF1-Fc-F1), but not inhibition of Ang2 improved blood brain barrier integrity and survival. It supported investigation of pro-Ang1, but not inhibition of Ang2 as adjunctive therapy for cerebral malaria. Further, it is of interest that Ang1-based treatment was efficacious and preserved blood brain barrier integrity, despite a robust systemic pro-inflammatory response to infection. The data suggest that anti-inflammatory strategies may not be required to preserve vascular integrity and improve outcome in life-threatening infections associated with systemic inflammation.

In one further experiment, AngF1-Fc-F1 will be administered in combination with an anti-Tie2 antibody (as set forth in US20130209492) to infected susceptible 057BI/6 mice to study the involvement of Tie2 in blocking the protective effect of AngF1-Fc-F1. The anti-Tie2 antibody may an activating (or agonist) antibody, e.g., it increases the binding of an angiopoietin and/or increases the activity of Tie2. It is expected that AngF1-Fc-F1 administered in combination with anti-Tie2 antibody will lead to lower survival of infected mice as compared to AngF1-Fc-F1 alone.

In another further experiment, AngF1-Fc-F1 will be used to treat resistant BALB/c mice infected with PbA to study the effect on survival, blood brain barrier integrity, neurological impairment, and plasma protein markers. It is expected that administration of AngF1-Fc-F1 will lead to improved protection of blood brain barrier integrity and survival of infected BALB/c mice.

In a third experiment, AngF1-Fc-F1 will be administered in combination with an anti-Tie2 antibody to infected resistant BALB/c mice to study if the resistant mice are rendered susceptible to ECM. It is expected that AngF1-Fc-F1 administered in combination with anti-Tie2 antibody will lead to lower survival of infected BALB/c mice as compared to AngF1-Fc-F1 alone.

Example 4: Therapeutic Administration of AngF1-Fc-F1 as Adjunctive Therapy in Combination with Artesunate In this Example, the effect of administration of Ang-F1-Fc-F1 in combination with artesunate on PbA-induced ECM in a mouse model was studied. Twenty 057BI/6 mice were infected by *Plasmodium berghei* ANKA (PbA) via an intraperitoneal injection of $1 \times 10^6$ freshly-isolated parasitized erythrocytes (PE) obtained from donor passage mice on Day 0. The infected mice were treated with 15 mg/kg of AngF1-Fc-F1 (SEQ ID NO: 2) on Days 4 and 6 post infection and with 10 mg/kg of artesunate on Day 5 post-infection via subcutaneous injection. The mice were monitored for survival, neurological impairment, parasite burden, and plasma protein levels, as described in detail in Example 1.

Figure 20:
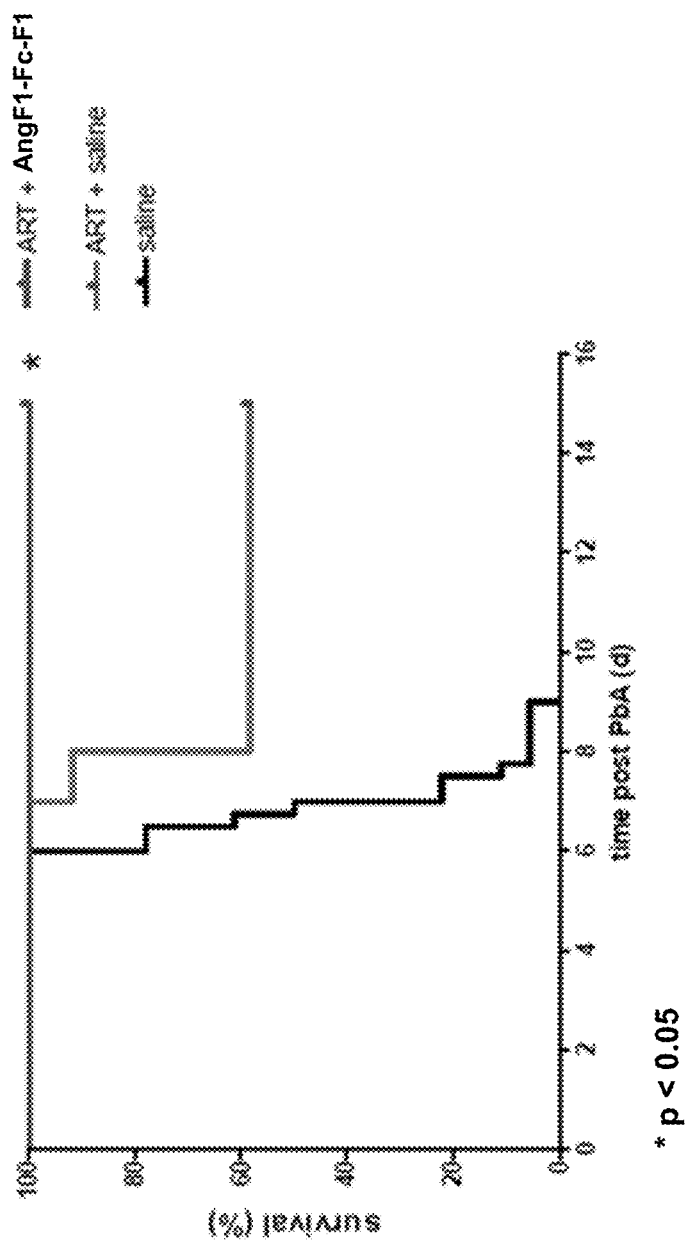
FIG. 20 shows survival curves of C57BI/6 mice infected with PbA and treated with artesunate+AngF1-Fc-F1, artesunate+saline, or saline.
Figure 21B:
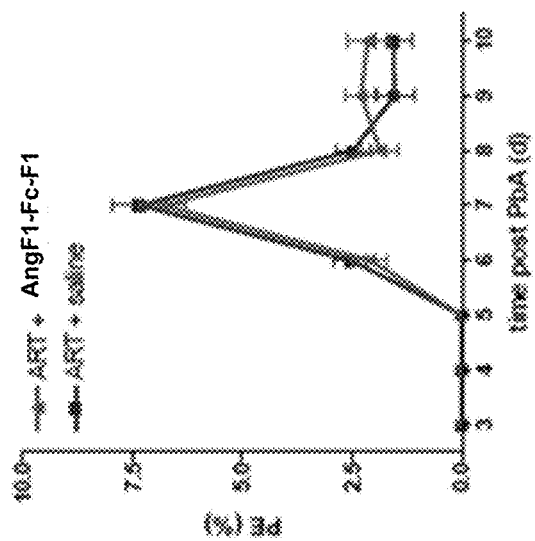
FIGS. 21(a) and 21(b)
Figure 21A:
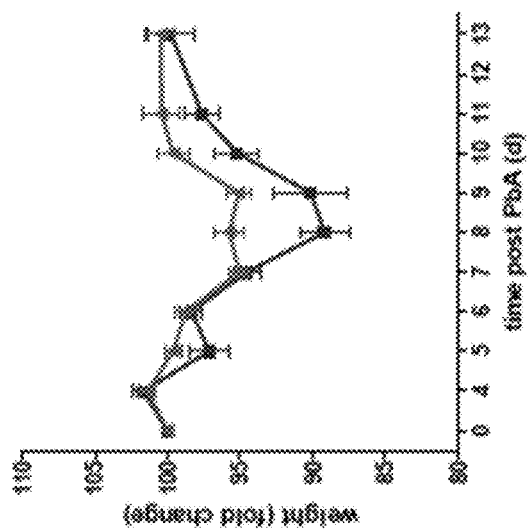

Adjunctive AngF1-Fc-F1 treatment significantly improved survival of infected mice as compared to artesunate alone (FIG. 20). Infected mice treated with AngF1-Fc-F1 in combination with artesunate showed 100% survival at least up to Day 15 post infection. In contrast, infected mice treated with artesunate alone showed less than 60% survival by Day 8 post infection. Despite significantly diminished parasite burden to pre-ECM levels (i.e., <2% parasitemia), 41.7% of artesunate treated mice died of ECM. This effect was independent of percent parasitemia (FIG. 21).

In a further experiment, the effect of adjunctive AngF1-Fc-F1 in combination with artesunate will be studied on neurological impairment in infected mice. It is expected that administration of AngF1-Fc-F1 in combination with artesunate will prevent neurological impairment in infected mice as compared to artesunate alone.

In another further experiment, AngF1-Fc-F1 will be administered in combination with an anti-Ang2 antibody (as described in Example 2) to study survival of infected mice. It is expected that AngF1-Fc-F1 administered in combination with anti-Ang2 antibody will lead to improved survival of infected mice as compared to AngF1-Fc-F1 alone.

Example 5: Protection from Malaria-Associated Acute Lung Injury

In this Example, the effect of AngF1-Fc-F1 administration on vascular permeability in lung and malaria-associated acute lung injury in infected mice will be studied. Twenty C57Bl/6 mice will be infected with *Plasmodium berghei* ANKA (PbA) via an intraperitoneal injection of $1\times10^6$ freshly-isolated parasitized erythrocytes (PE) obtained from donor passage mice on Day 0. The infected mice will be treated with 15 mg/kg of AngF1-Fc-F1 (SEQ ID NO: 2) on Days 4, and 6 post-infection via subcutaneous injection. The mice will be monitored for survival and vascular permeability in lung by Evans Blue staining.

It is expected that mice treated with AngF1-Fc-F1 will show absence of Evans Blue dye uptake in lungs pointing to absence of vascular permeability and protection from malaria-associated acute lung injury.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of preventing vascular leakage or protecting blood brain barrier integrity, the method comprising administering a pharmaceutical composition comprising a therapeutically effective amount of a fusion protein comprising at least one fibrinogen-like domain of angiopoietin-1 fused to an immunoglobulin Fc fragment to a subject in need thereof.

2. The method of claim 1, wherein the subject suffers from a disease or disorder selected from the group consisting of severe cerebral malaria, experimental cerebral malaria, sepsis, dengue, hemorrhagic fever, toxic shock syndrome, hemorrhagic shock, hemolytic uremic syndrome, myocardial infarction and stroke.

3. The method of claim 1, wherein the subject is infected with *Plasmodium* spp.

4. The method of claim 1, wherein the fusion protein is administered at a dose of 15 mg/kg of the subject's body weight.

5. The method of claim 1, wherein the fusion protein is administered subcutaneously.

6. The method of claim 1, wherein the fusion protein is administered in combination with a second therapeutic agent.

7. The method of claim 6, wherein the second therapeutic agent is artesunate.

8. The method of claim 1, wherein the fusion protein comprises a first fibrinogen-like domain of angiopoietin-1 fused at its C-terminal end to the N-terminal end of an Fc fragment and the Fc fragment fused at its C-terminal end to the N-terminal end of a second fibrinogen-like domain of angiopoietin-1.

9. The method of claim 1, wherein the fusion protein is AngF1-Fc-F1.

10. The method of claim 1, wherein the fusion protein comprises the amino acid sequence of SEQ ID NO: 2.

11. The method of claim 10, wherein the fusion protein consists of the amino acid sequence of SEQ ID NO: 2.

12. The method of claim 1, wherein the fusion protein is a dimer comprising a first AngF1-Fc-F1 and a second AngF1-Fc-F1, wherein the first and second AngF1-Fc-F1s associate through intramolecular association of the Fc fragments.

13. The method of claim 1, wherein the Fc fragment is an IgG Fc domain.

14. The method of claim 13, wherein the Fc fragment is a human IgG1 Fc domain.

15. The method of claim 3, wherein the method comprises preventing vascular leakage in a subject infected with *plasmodium falciparum*.

16. The method of claim 3, wherein the method comprises protecting blood brain barrier integrity in a subject infected with *plasmodium falciparum*.

\* \* \* \* \*

SEQUENCE LISTING

```
<160> NUMBER OF SEQ ID NOS: 4

<210> SEQ ID NO 1
<211> LENGTH: 1977
<212> TYPE: DNA
<213> ORGANISM: Artificial Sequence
<220> FEATURE:
<223> OTHER INFORMATION: synthetic

<400> SEQUENCE: 1
ttcagagact gcgccgacgt gtaccaggcc ggcttcaaca agtccggcat ctacaccatc      60
tacatcaaca acatgcctga gcctaagaag gtgttctgca acatggacgt gaacggcggc     120
ggctggacag tgatccagca cagagaggac ggctccctgg acttccagag aggctggaag     180
gagtacaaga tgggcttcgg caacccttcc ggcgagtact ggctgggcaa cgagttcatc     240
ttcgccatca cctcccagag acagtacatg ctgagaatcg agctgatgga ctgggagggc     300
aacagagcct actcccagta cgacagattc cacatcggca acgagaagca gaactacaga     360
ctgtacctga agggccacac cggcaccgcc ggcaagcagt cctccctgat cctccacggc     420
gccgacttct ccaccaagga cgccgacaac gacaactgca tgtgcaagtg cgccctgatg     480
ctgaccggcg gctggtggtt cgacgcctgc ggcccttcca acctgaacgg catgttctac     540
accgccggcc agaaccacgg caagctgaac ggcatcaagt ggcactactt caaaggcccc     600 cctactccc tgaggtcgac caccatgatg atcagacctc tggacttcga caaaactcac      660
acatgcccac cgtgccagc acctgaactc ctggggggac cgtcagtctt cctcttcccc      720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg caaggtctcc     960
aacaaagccc tcccagcccc catcgagaaa accatctcca aagccaaagg gcagccccga    1020
gaaccacagg tgtacaccct gcccccatcc cgggatgagc tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctata gcaagctcac cgtggacaag agcaggtggc agcagggaa cgtcttctca     1260 tgctccgtga tgcatgaggc tctgcacaac cactacacgc agaagagcct ctccctgtct    1320
ccgggtttta gagactgcgc agatgtatat caagctggtt taataaaag tggaatctac    1380 actatttata ttaataatat gccagaaccc aaaaaggtgt tttgcaatat ggatgtcaat    1440
gggggaggtt ggactgtaat acaacatcgt gaagatggaa gtctagattt ccaaagaggc    1500
tggaaggaat ataaaatggg ttttggaaat ccctccggtg aatattggct ggggaatgag    1560
```

-continued

```
tttattttg ccattaccag tcagaggcag tacatgctaa gaattgagtt aatggactgg    1620
gaagggaacc gagcctattc acagtatgac agattccaca taggaaatga aaagcaaaac    1680
tataggttgt atttaaaagg tcacactggg acagcaggaa acagagcag cctgatctta     1740 cacggtgctg atttcagcac taaagatgct gataatgaca actgtatgtg caaatgtgcc    1800
ctcatgttaa caggaggatg gtggtttgat gcttgtggcc cctccaatct aaatggaatg    1860
ttctatactg cgggacaaaa ccatggaaaa ctgaatggga taaagtggca ctacttcaaa    1920
gggccaagtt actccttacg ttccacaact atgatgattc gacctttaga tttttaa      1977
```

<210> SEQ ID NO 2
<211> LENGTH: 658
<212> TYPE: PRT
<213> ORGANISM: Artificial Sequence
<220> FEATURE:
<223> OTHER INFORMATION: synthetic

<400> SEQUENCE: 2

```
Phe Arg Asp Cys Ala Asp Val Tyr Gln Ala Gly Phe Asn Lys Ser Gly
  1               5                  10                  15

Ile Tyr Thr Ile Tyr Ile Asn Asn Met Pro Glu Pro Lys Lys Val Phe
             20                  25                  30

Cys Asn Met Asp Val Asn Gly Gly Gly Trp Thr Val Ile Gln His Arg
         35                  40                  45

Glu Asp Gly Ser Leu Asp Phe Gln Arg Gly Trp Lys Glu Tyr Lys Met
     50                  55                  60

Gly Phe Gly Asn Pro Ser Gly Glu Tyr Trp Leu Gly Asn Glu Phe Ile
 65                  70                  75                  80

Phe Ala Ile Thr Ser Gln Arg Gln Tyr Met Leu Arg Ile Glu Leu Met
                 85                  90                  95

Asp Trp Glu Gly Asn Arg Ala Tyr Ser Gln Tyr Asp Arg Phe His Ile
            100                 105                 110

Gly Asn Glu Lys Gln Asn Tyr Arg Leu Tyr Leu Lys Gly His Thr Gly
        115                 120                 125

Thr Ala Gly Lys Gln Ser Ser Leu Ile Leu His Gly Ala Asp Phe Ser
    130                 135                 140

Thr Lys Asp Ala Asp Asn Asp Asn Cys Met Cys Lys Cys Ala Leu Met
145                 150                 155                 160

Leu Thr Gly Gly Trp Trp Phe Asp Ala Cys Gly Pro Ser Asn Leu Asn
                165                 170                 175

Gly Met Phe Tyr Thr Ala Gly Gln Asn His Gly Lys Leu Asn Gly Ile
            180                 185                 190

Lys Trp His Tyr Phe Lys Gly Pro Ser Tyr Ser Leu Arg Ser Thr Thr
        195                 200                 205

Met Met Ile Arg Pro Leu Asp Phe Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
```

```
            290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Phe Arg Asp Cys Ala Asp
        435                 440                 445
Val Tyr Gln Ala Gly Phe Asn Lys Ser Gly Ile Tyr Thr Ile Tyr Ile
450                 455                 460
Asn Asn Met Pro Glu Pro Lys Lys Val Phe Cys Asn Met Asp Val Asn
465                 470                 475                 480
Gly Gly Gly Trp Thr Val Ile Gln His Arg Glu Asp Gly Ser Leu Asp
                485                 490                 495
Phe Gln Arg Gly Trp Lys Glu Tyr Lys Met Gly Phe Gly Asn Pro Ser
            500                 505                 510
Gly Glu Tyr Trp Leu Gly Asn Glu Phe Ile Phe Ala Ile Thr Ser Gln
        515                 520                 525
Arg Gln Tyr Met Leu Arg Ile Glu Leu Met Asp Trp Glu Gly Asn Arg
530                 535                 540
Ala Tyr Ser Gln Tyr Asp Arg Phe His Ile Gly Asn Glu Lys Gln Asn
545                 550                 555                 560
Tyr Arg Leu Tyr Leu Lys Gly His Thr Gly Thr Ala Gly Lys Gln Ser
                565                 570                 575
Ser Leu Ile Leu His Gly Ala Asp Phe Ser Thr Lys Asp Ala Asp Asn
            580                 585                 590
Asp Asn Cys Met Cys Lys Cys Ala Leu Met Leu Thr Gly Gly Trp Trp
        595                 600                 605
Phe Asp Ala Cys Gly Pro Ser Asn Leu Asn Gly Met Phe Tyr Thr Ala
610                 615                 620
Gly Gln Asn His Gly Lys Leu Asn Gly Ile Lys Trp His Tyr Phe Lys
625                 630                 635                 640
Gly Pro Ser Tyr Ser Leu Arg Ser Thr Thr Met Met Ile Arg Pro Leu
                645                 650                 655
Asp Phe

<210> SEQ ID NO 3
<211> LENGTH: 2025
<212> TYPE: DNA
<213> ORGANISM: Artificial Sequence
<220> FEATURE:
<223> OTHER INFORMATION: synthetic

<400> SEQUENCE: 3
```

```
agagactgtg ctgaagtatt caaatcagga cacaccacaa atggcatcta cacgttaaca      60
ttccctaatt ctacagaaga gatcaaggcc tactgtgaca tggaagctgg aggaggcggg     120
tggacaatta ttcagcgacg tgaggatggc agcgttgatt ttcagaggac ttggaaagaa     180
tataaagtgg gatttggtaa cccttcagga gaatattggc tgggaaatga gtttgtttcg     240
caactgacta atcagcaacg ctatgtgctt aaaatacacc ttaaagactg gaagggaat      300 gaggcttact cattgtatga acatttctat ctctcaagtg aagaactcaa ttataggatt     360
caccttaaag gacttacagg gacagccggc aaaataagca gcatcagcca accaggaaat     420
gattttagca caaaggatgg agacaacgac aaatgtattt gcaaatgttc acaaatgcta     480
acaggaggct ggtggtttga tgcatgtggt ccttccaact gaacggaat gtactatcca     540 cagaggcaga acacaaataa gttcaacggc attaaatggt actactggaa aggctcaggc     600
tattcgctca aggccacaac catgatgatc cgaccagcag atttcggggg cccgggcgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc      780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaaggcggtg cggttctgg cgcgcctaga    1380 gactgtgctg aagtattcaa atcaggacac accacaaatg catctacac gttaacattc     1440 cctaattcta cagaagagat caaggcctac tgtgacatgg aagctggagg aggcgggtgg    1500
acaattattc agcgacgtga ggatggcagc gttgatttc agaggacttg aaagaatat    1560 aaagtgggat ttggtaaccc ttcaggagaa tattggctgg gaaatgagtt tgtttcgcaa    1620
ctgactaatc agcaacgcta tgtgcttaaa atacacctta agactggga agggaatgag    1680 gcttactcat tgtatgaaca tttctatctc tcaagtgaag aactcaatta taggattcac    1740
cttaaaggac ttacagggac agccggcaaa ataagcagca tcagccaacc aggaaatgat    1800
tttagcacaa aggatggaga caacgacaaa tgtatttgca aatgttcaca aatgctaaca    1860
ggaggctggt ggtttgatgc atgtggtcct tccaacttga acggaatgta ctatccacag    1920
aggcagaaca caaataagtt caacggcatt aaatggtact actggaaagg ctcaggctat    1980
tcgctcaagg ccacaaccat gatgatccga ccagcagatt tctga                    2025
```

<210> SEQ ID NO 4  
<211> LENGTH: 674  
<212> TYPE: PRT  
<213> ORGANISM: Artificial Sequence  
<220> FEATURE:  
<223> OTHER INFORMATION: synthetic

<400> SEQUENCE: 4

```
Arg Asp Cys Ala Glu Val Phe Lys Ser Gly His Thr Thr Asn Gly Ile
  1               5                  10                 15

Tyr Thr Leu Thr Phe Pro Asn Ser Thr Glu Glu Ile Lys Ala Tyr Cys
             20                  25                 30

Asp Met Glu Ala Gly Gly Gly Trp Thr Ile Ile Gln Arg Arg Glu
             35              40                  45

Asp Gly Ser Val Asp Phe Gln Arg Thr Trp Lys Glu Tyr Lys Val Gly
 50                  55                  60

Phe Gly Asn Pro Ser Gly Glu Tyr Trp Leu Gly Asn Glu Phe Val Ser
 65                  70                  75                 80

Gln Leu Thr Asn Gln Gln Arg Tyr Val Leu Lys Ile His Leu Lys Asp
                 85                  90                 95

Trp Glu Gly Asn Glu Ala Tyr Ser Leu Tyr Glu His Phe Tyr Leu Ser
                100                 105                110

Ser Glu Glu Leu Asn Tyr Arg Ile His Leu Lys Gly Leu Thr Gly Thr
            115                 120                 125

Ala Gly Lys Ile Ser Ser Ile Ser Gln Pro Gly Asn Asp Phe Ser Thr
        130                 135                 140

Lys Asp Gly Asp Asn Asp Lys Cys Ile Cys Lys Cys Ser Gln Met Leu
145                 150                 155                160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe Gly Gly Pro Gly Glu Pro Lys Ser Cys
    210                 215                 220

Asp Lys Thr His Thr Cys Pro Pro Cys Pro Ala Pro Glu Leu Leu Gly
225                 230                 235                240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
                    420                 425                 430
His Glu Ala Leu His Asn His Tyr Thr Gln Lys Ser Leu Ser Leu Ser
            435                 440                 445

Pro Gly Lys Gly Gly Gly Ser Gly Ala Pro Arg Asp Cys Ala Glu
            450                 455                 460

Val Phe Lys Ser Gly His Thr Thr Asn Gly Ile Tyr Thr Leu Thr Phe
465             470                 475                 480

Pro Asn Ser Thr Glu Glu Ile Lys Ala Tyr Cys Asp Met Glu Ala Gly
                485                 490                 495

Gly Gly Gly Trp Thr Ile Ile Gln Arg Arg Glu Asp Gly Ser Val Asp
            500                 505                 510

Phe Gln Arg Thr Trp Lys Glu Tyr Lys Val Gly Phe Gly Asn Pro Ser
            515                 520                 525

Gly Glu Tyr Trp Leu Gly Asn Glu Phe Val Ser Gln Leu Thr Asn Gln
            530                 535                 540

Gln Arg Tyr Val Leu Lys Ile His Leu Lys Asp Trp Glu Gly Asn Glu
545                 550                 555                 560

Ala Tyr Ser Leu Tyr Glu His Phe Tyr Leu Ser Ser Glu Glu Leu Asn
                565                 570                 575

Tyr Arg Ile His Leu Lys Gly Leu Thr Gly Thr Ala Gly Lys Ile Ser
            580                 585                 590

Ser Ile Ser Gln Pro Gly Asn Asp Phe Ser Thr Lys Asp Gly Asp Asn
            595                 600                 605

Asp Lys Cys Ile Cys Lys Cys Ser Gln Met Leu Thr Gly Gly Trp Trp
            610                 615                 620

Phe Asp Ala Cys Gly Pro Ser Asn Leu Asn Gly Met Tyr Tyr Pro Gln
625             630                 635                 640

Arg Gln Asn Thr Asn Lys Phe Asn Gly Ile Lys Trp Tyr Tyr Trp Lys
                645                 650                 655

Gly Ser Gly Tyr Ser Leu Lys Ala Thr Thr Met Met Ile Arg Pro Ala
                660                 665                 670

Asp Phe
```